United States Patent
May et al.

(10) Patent No.: US 11,552,010 B2
(45) Date of Patent: Jan. 10, 2023

(54) DIELECTRIC FOR HIGH DENSITY SUBSTRATE INTERCONNECTS

(71) Applicant: Intel Corporation, Santa Clara, CA (US)

(72) Inventors: Robert A. May, Chandler, AZ (US); Andrew J. Brown, Chandler, AZ (US); Sri Ranga Sai Boyapati, Chandler, AZ (US); Kristof Darmawikarta, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 482 days.

(21) Appl. No.: 16/603,863

(22) PCT Filed: May 12, 2017

(86) PCT No.: PCT/US2017/032436
§ 371 (c)(1),
(2) Date: Oct. 9, 2019

(87) PCT Pub. No.: WO2018/208317
PCT Pub. Date: Nov. 15, 2018

(65) Prior Publication Data
US 2020/0118917 A1 Apr. 16, 2020

(51) Int. Cl.
*H01L 23/498* (2006.01)
*C07D 413/12* (2006.01)
(Continued)

(52) U.S. Cl.
CPC ...... *H01L 23/49894* (2013.01); *C07D 413/12* (2013.01); *C08G 73/16* (2013.01);
(Continued)

(58) Field of Classification Search
CPC ......... H01L 23/49894; H01L 23/49822; H01L 23/49838; H01L 21/4857; C08K 3/22; C08K 3/38; C08K 13/02; C07D 413/12
See application file for complete search history.

(56) References Cited

U.S. PATENT DOCUMENTS

| 5,015,719 A | 5/1991 | Papathomas et al. |
| 5,147,518 A | 9/1992 | Freilich |

(Continued)

FOREIGN PATENT DOCUMENTS

| JP | 08-283409 | 10/1996 |
| JP | 09-104753 | 4/1997 |
| JP | 2012014843 | 1/2012 |

OTHER PUBLICATIONS

International Search Report and Written Opinion from related PCT/US2017/032436 dated Feb. 9, 2018.
(Continued)

*Primary Examiner* — Jasmine J Clark
(74) *Attorney, Agent, or Firm* — Schwabe, Williamson & Wyatt, P.C.

(57) ABSTRACT

The present disclosure is directed to systems and methods for providing a dielectric layer on a semiconductor substrate capable of supporting very high density interconnects (i.e., ≥100 IO/mm). The dielectric layer includes a maleimide polymer in which a thiol-terminated functional group cross-links with an epoxy resin. The resultant dielectric material provides a dielectric constant of less than 3 and a dissipation factor of less than 0.001. Additionally, the thiol functional group forms coordination complexes with noble metals present in the conductive structures, thus by controlling the stoichiometry of epoxy to polyimide, the thiol-polyimide may beneficially provide an adhesion enhancer between the dielectric and noble metal conductive structures.

25 Claims, 4 Drawing Sheets

(51) Int. Cl.
  *C08G 73/16* (2006.01)
  *C08K 3/22* (2006.01)
  *C08K 3/38* (2006.01)
  *C08K 5/548* (2006.01)
  *C08K 13/02* (2006.01)
  *H01L 21/48* (2006.01)

(52) U.S. Cl.
  CPC .................. *C08K 3/22* (2013.01); *C08K 3/38* (2013.01); *C08K 5/548* (2013.01); *C08K 13/02* (2013.01); *H01L 21/4857* (2013.01); *H01L 23/49822* (2013.01); *H01L 23/49838* (2013.01); C08K 2003/2258 (2013.01); C08K 2003/385 (2013.01)

(56) References Cited

U.S. PATENT DOCUMENTS

| | | | | |
|---|---|---|---|---|
| 8,223,472 B1* | 7/2012 | Dirk | ................. | H01G 4/18 |
| | | | | 361/313 |
| 2004/0038021 A1* | 2/2004 | Nagai | ................. | H01L 23/5329 |
| | | | | 428/209 |
| 2012/0125664 A1* | 5/2012 | Niemi | ................. | H05K 3/4694 |
| | | | | 174/250 |

OTHER PUBLICATIONS

International Preliminary Report on Patentability from related PCT/US2017/032436 dated Nov. 12, 2019.

* cited by examiner

DIELECTRIC FOR HIGH DENSITY SUBSTRATE INTERCONNECTS

CROSS-REFERENCE TO RELATED APPLICATIONS

This patent application is a U.S. National Phase Application under 35 U.S.C. § 371 of International Application No. PCT/US2017/032436, filed on May 12, 2017, the entire contents of which is hereby incorporated by reference herein.

TECHNICAL FIELD

The present disclosure relates to dielectric materials used in the fabrication of semiconductor substrates.

BACKGROUND

High Density Interconnect ("HDI") printed circuit boards ("PCBs") take advantage of the decreasing size of components, such as semiconductor dies, and the resultant increase in interconnect density to effectively reduce the board area needed by each component to a minimum. Thus, small form factor devices such as smartphones and many Internet of Things (IoT) devices may benefit from the use of HDI PCBs.

HDI between semiconductor die and a substrate facilitate advancements in high performance computing. Typical applications such as the interconnection of logic die to high bandwidth memory, logic die stitching, and high bandwidth system-in-package ("SiP"—several integrated circuits disposed in a single module or package) integration may have input/output ("I/O") densities that exceed 100 I/O points per millimeter (IO/mm). Such high I/O densities exceed existing substrate packaging solutions which typically accommodate about 50 IO/mm.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

Figure 1:
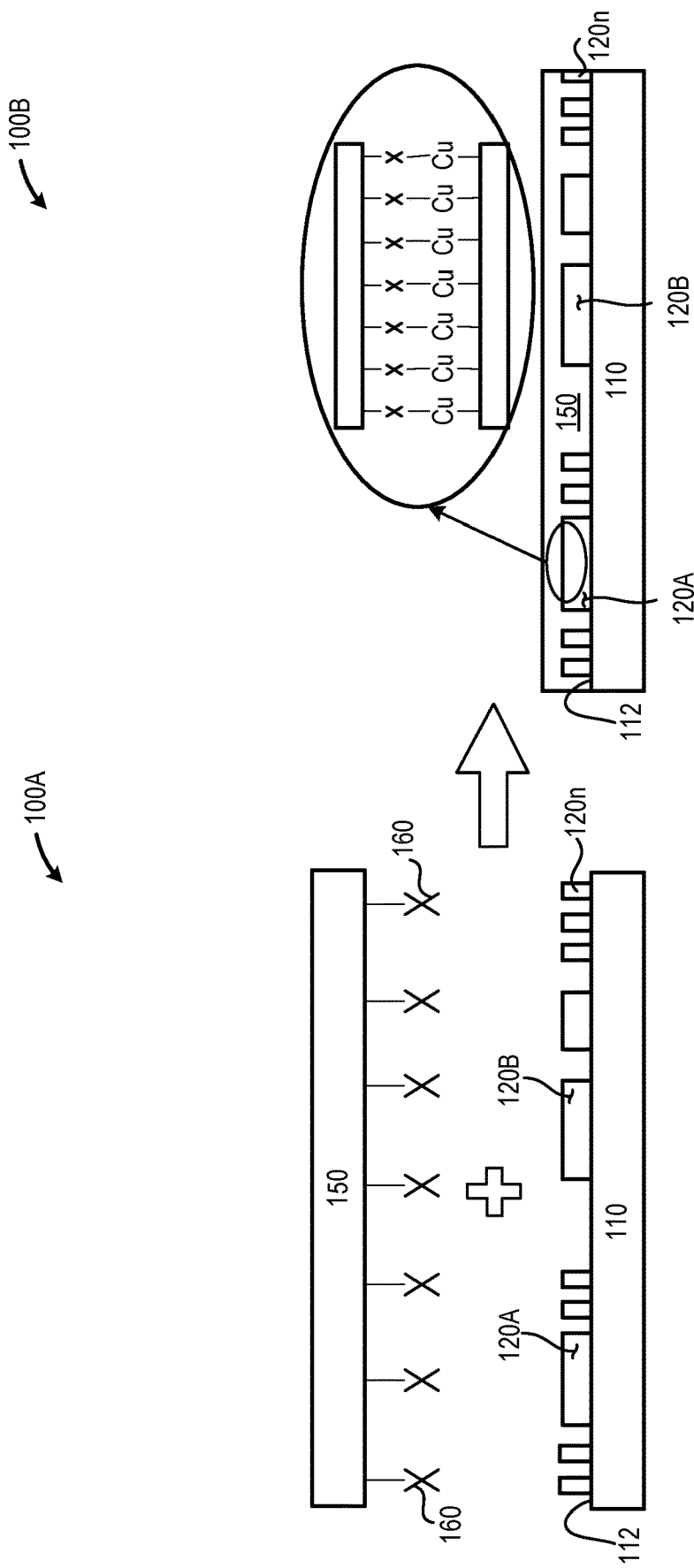
FIG. 1A is a partial cross-sectional elevation of an illustrative system prior to chemically bonding a dielectric layer to a substrate that includes a plurality of conductive structures, in accordance with at least one embodiment described herein.
FIG. 1B is a partial cross-sectional elevation of the illustrative system depicted in FIG. 1A after the pendant groups in the dielectric layer chemically bond to at least one of the substrate and/or at least some of the plurality of conductive structures, in accordance with at least one embodiment described herein.

Although the following Detailed Description will proceed with reference being made to illustrative embodiments, many alternatives, modifications and variations thereof will be apparent to those skilled in the art.

DETAILED DESCRIPTION

The dielectric constant ("Dk") of a material is a measure of an insulators ability to store electrical energy. The dielectric constant is the ratio of the capacitance induced by two metallic plates with an insulator between them to the capacitance of the same plates with air or a vacuum between them. The dissipation factor ("Df") is defined as the reciprocal of the ratio between the insulating materials capacitive reactance to its resistance at a specified frequency. It measures the inefficiency of an insulating material.

Many options for very high density ("VHD") I/O (i.e., I/O densities at or above 100 IO/mm) interconnects frequently have undesirable material properties. For example, traditional silicon interposer and embedded interconnect bridge ("EMIB") technologies employ wafer technologies having very high dielectric constants—about 7.5 for silicon nitride ($Si_3N_4$) and about 3.9 for silicon oxide ($SiO_2$). The use of such high dielectric constant materials adversely impacts electrical performance by increasing parasitic losses attributable to system capacitance. At high frequencies and in the presence of high I/O densities characteristic of VHD routing applications, such capacitive losses are particularly detrimental to system performance.

Another option is an "organic interposer" formed using photo-imagable dielectrics ("PID"). However, the materials used in PID typically have very high coefficients of thermal expansion ("CTE"), which frequently exceed 50 ppm. Further, the materials used in PID typically have high moisture absorption that negatively impact physical strength and mechanical reliability. Additionally, the materials used in PID are typically poor electromigration barriers bringing into question the long-term electrical reliability of such materials.

The systems and methods described herein facilitate the use of high density I/O interconnects by providing a dielectric material having a relatively low dielectric constant (e.g., less than 3) and a relatively low dissipation factor (e.g., less than 0.001). The systems and methods described herein provide materials useful in forming VHD interconnects. The materials have favorable features such as: an integral adhesion promoter to copper structures; low surface roughness to support photolithographic patterning of ultra-fine pitch routing; mechanical stability that provides physical reliability; and properties that provide an effective electromigration barrier.

The systems and methods described herein provide materials that make use of: additives capable of chemically bonding to the noble metal conductive structures (e.g., copper traces); one or more nanofillers having a low dielectric constant; and a resin system that includes a cyanate ester (a chemical substance in which the hydrogen atom of the phenolic OH group is substituted by a cyanide group), bisphenol AF (a fluorinated organic compound related to bisphenol A in which the two methyl groups are replaced with trifluoromethyl groups), and a polyimide (a polymer of imide monomers). The materials disclosed herein may be used in conjunction with a primer layer that enables the revealing of embedded noble metal conductive structures.

The systems and methods disclosed herein beneficially and advantageously provide materials that obviate the use of laser methods to open or otherwise form vias through the resin layer. The systems and methods disclosed herein offset the high coefficient of thermal expansion and low modulus inherent in such resin systems—i.e., the fact that nonpolar compounds exhibit weak intramolecular forces and low crosslinking capabilities—through a unique combination of adhesion/crosslinking capabilities along with a filler system. The systems and methods described herein provide polymer nanocomposite systems that are compatible with very high density I/O applications.

A semiconductor substrate is provided. The semiconductor substrate may include: a substrate having a first surface; at least one conductive structure disposed on at least a portion of the first surface of the substrate; and a dielectric layer disposed across at least a portion of the first surface of the substrate and the at least one conductive structure, the dielectric layer having a dielectric constant (Dk) of less than or equal to 3 and a dissipation factor (DO of less than or equal to 0.001.

A method of fabricating a semiconductor substrate is provided. The method may include: patterning at least one conductive structure on a first surface of a substrate; and disposing a dielectric layer having a dielectric constant (Dk) of less than or equal to 3 and a dissipation factor (DO of less than or equal to 0.001 across at least a portion of the substrate and the at least one conductive structure.

A dielectric material is provided. The dielectric material may have a dielectric constant (Dk) of less than or equal to 3 and a dissipation factor (DO of less than or equal to 0.001 and comprising a compound that includes at least one of:

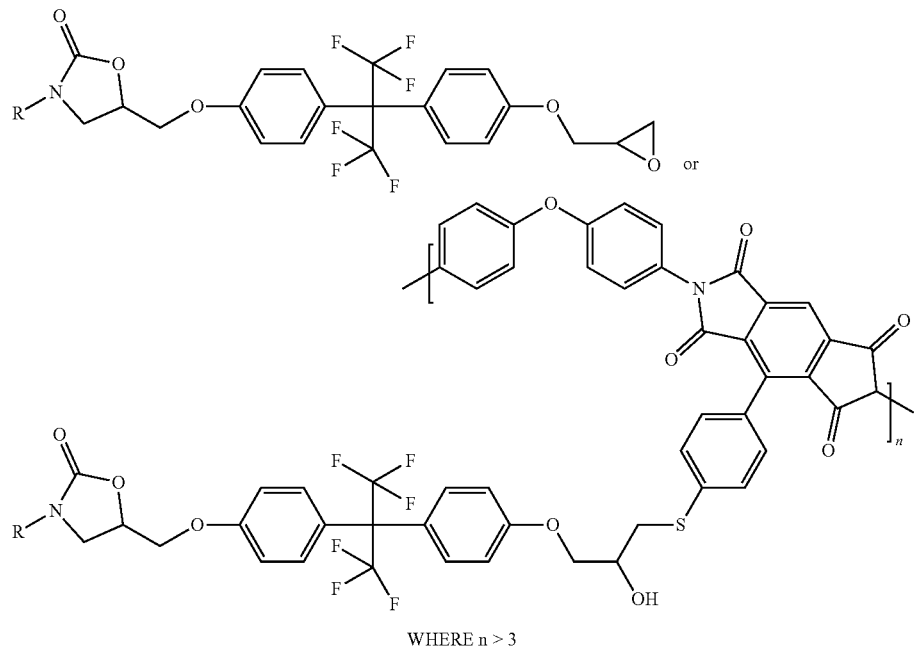

WHERE n > 3

As used herein the terms "top," "bottom," "lowermost," and "uppermost" when used in relationship to one or more elements are intended to convey a relative rather than absolute physical configuration. Thus, an element described as an "uppermost element" or a "top element" in a device may instead form the "lowermost element" or "bottom element" in the device when the device is inverted. Similarly, an element described as the "lowermost element" or "bottom element" in the device may instead form the "uppermost element" or "top element" in the device when the device is inverted.

As used herein, the term "logically associated" when used to refer to various objects, systems, or elements, is intended to convey the existence of a relationship between the objects, systems, or elements such that access to one object, system, or element exposes the remaining objects, systems, or elements having a "logical association" with or to the accessed object, system, or element. An example "logical association" exists between relational databases where access to an element in a first database may provide information and/or data from one or more elements in one or more additional databases, each having an identified relationship to the accessed element. In another example, if "A"

is logically associated with "B," accessing "A" will expose or otherwise draw information and/or data from "B," and vice-versa.

As used herein, the term "motherboard" is used in a relative rather than absolute sense in that the "motherboard" refers to the substrate to which a semiconductor package is attached. Thus, the "motherboard" may, in some instances, include a true motherboard in the sense that a central processing unit is communicably coupled to the substrate. In other instances, the "motherboard" may include any substrate to which the semiconductor package is attached, including, but not limited to, daughter boards, peripheral boards, graphics cards, and similar.

FIG. 1A is a partial cross-sectional elevation of an illustrative system 100A prior to chemically bonding a dielectric layer 150 to a substrate 110 that includes a plurality of conductive structures 120A-120n (collectively, "conductive structures 120"), in accordance with at least one embodiment described herein. FIG. 1B is a partial cross-sectional elevation of an illustrative system 100B after the pendant groups 160 in the dielectric layer 150 chemically bond to at least one of the substrate 110 and/or at least some of the plurality of conductive structures 120, in accordance with at least one embodiment described herein.

The dielectric layer 150 may have physical and/or electrical properties that improve the performance, reliability, and/or capability of the substrate 110 and/or one or more devices and/or systems coupled to the substrate 110. For example, the dielectric layer may include one or more materials having a low dielectric constant ("Dk"—for example, a dielectric constant of less than or equal to 3). The dielectric layer 150 may include one or more adhesion promoters that improve the bonding between the dielectric layer 150, the substrate 110, and/or the conductive structures 120. In embodiments, the finished dielectric layer 150 is sufficiently smooth to support patterning an ultra-fine pitch routing (e.g., a pitch routing of at least 100 input/outputs per millimeter or "IO/mm"). In embodiments, the dielectric layer 150 provides mechanical stability for the substrate, improving the reliability of the device and/or system using the substrate. In embodiments, the dielectric layer 150 beneficially prevents electromigration between conductive structures 120 disposed on the first surface of the substrate 110. The physical and electrical properties of the dielectric layer 150 beneficially improve the mechanical reliability of the substrate 110 and the devices mounted thereupon, and beneficially facilitate the use of ultra-fine pitch connector arrays, fine conductive structures (e.g., transmission lines having widths of 5 micrometers or less), and closely spaced conductive structures 120.

The substrate 110 may include any currently available or future developed material capable of supporting or otherwise accommodating the conductive structure 120. In some implementations, the substrate 110 may include a laminated structure containing at least one conductive layer disposed between a plurality of nonconductive or dielectric layers. In some implementations, the substrate may include one or more motherboards, daughterboards, expansion cards, or similar structures that carry one or more semiconductor packages. The substrate 110 may have any size, shape, or physical configuration. Although the conductive structures 120 are depicted as deposited only on the first surface 112 of the substrate 110, in embodiments, the conductive structures may be deposited on one or more additional surfaces of the substrate 110.

The conductive structures 120 may have any size, shape, or physical configuration. The conductive structures conductively couple one or more electrical components, semiconductor devices, and/or logic elements disposed in the, on, or about the substrate 110 to each other and/or to one or more surface-mount, socket-mount, or pin-mount devices, semiconductor packages, and/or components distributed on the first surface 112 of the substrate 110. In embodiments, the dielectric layer 150 disclosed herein beneficially permits the use of conductive structures, such as transmission lines, having a width of about 3 micrometers ($\mu m$) or less; about 5 $\mu m$ or less; about 7 $\mu m$ or less; or about 10 $\mu m$ or less. In embodiments, the dielectric layer 150 disclosed herein beneficially permits the spacing between neighboring conductive structures 120 of about: 10 micrometers ($\mu m$) or less; about 7 $\mu m$ or less; about 5 $\mu m$ or less; or about 3 $\mu m$ or less.

In some implementations, at least some of the conductive structures 120 may include a plurality of conductive structures, each fabricated using the same electrically conductive material. In other implementations, at least some of the conductive structures 120 may include a plurality of conductive structures, each fabricated using different electrically conductive materials. Example metallic materials useful for providing, fabricating, forming, depositing, and/or patterning at least some of the conductive structures 120 include, but are not limited to: copper and/or copper-containing alloys; silver and/or silver-containing alloys; gold and/or gold-containing alloys; tin and/or tin-containing alloys; nickel and/or nickel-containing alloys; or aluminum and/or aluminum-containing alloys. Example non-metallic materials useful for providing, fabricating, forming, depositing, and/or patterning at least some of the conductive structures 120 include, but are not limited to: electrically conductive polymers; graphene; and similar.

The conductive structures 120 may be placed, deposited, formed, or otherwise patterned on the surface 112 of the substrate 110 using any currently available or future developed deposition method. In embodiments, the conductive structures 120 may include copper/copper alloy structures that are photolithographically deposited on the first surface 112 of the substrate 110. In embodiments, the conductive structures 120 may include copper/copper alloy structures 120 that are electrolytically plated on the first surface 112 of the substrate 110. In embodiments, the conductive structures 120 may include copper/copper alloy structures dispersed in a resin or similar carrier fluid that is printed on the first surface 112 of the substrate 110. In some implementations, at least a portion of the conductive structures 120 may include three-dimensional conductive structures 120 that project a distance above the first surface 112 of the substrate 110.

The dielectric layer 150 includes one or more resins or similar substances capable of providing insulation between the conductive structures 120 on the first surface 112 of the substrate 110. In embodiments, the dielectric layer 150 may be applied to the substrate 110 and the conductive structures 120 using any currently available or future developed techniques. In some implementations, the dielectric layer 150 may be formed, applied, deposited, or otherwise disposed as a softened solid sheet (e.g., a solid sheet softened by exposure to temperatures greater than ambient temperature) across all or a portion of the substrate 110 and conductive structure 120. In some implementations, the dielectric layer 150 may be applied, deposited, or otherwise disposed as a liquid across all or a portion of the substrate 110 and conductive structure 120 via spin application, spray application, inkjet printing, or any other currently available or future developed deposition technique.

In embodiments, the dielectric layer 150 may have a uniform thickness across at least a portion of the substrate 110 and conductive structures 120. Such a uniform thickness dielectric layer 150 would follow the surface contours/surface profile of the conductive structures on the first surface 112 of the substrate 110. In embodiments, the dielectric layer 150 may have a non-uniform thickness across at least a portion of the substrate 110 and conductive structures 120. In such embodiments, the exposed surface of the dielectric layer 150 may be finished to provide a surface having a roughness (Ra) of: less than about 1 micrometer (μm); less than about 800 nanometers (nm); less than about 600 nm; less than about 400 nm; less than about 200 nm; or less than about 100 nm. The dielectric layer 150 may be surface finished to provide an acceptable level of roughness using any currently available or future developed surface finishing technique including, but not limited to: chemical/mechanical planarization ("CMP"); grinding; polishing; lapping; and similar. In embodiments, the dielectric layer 150 may have a thickness of: about 10 micrometers (μm) or less; about 7 μm or less; about 5 μm or less; about 3 μm or less; or about 2 μm or less. In embodiments, the dielectric layer 150 may have an average thickness of: about 10 micrometers (μm) or less; about 7 μm or less; about 5 μm or less; about 3 μm or less; or about 2 μm or less. In embodiments, the dielectric layer 150 may have a maximum thickness of: about 10 micrometers (μm) or less; about 7 μm or less; about 5 μm or less; about 3 μm or less; or about 2 μm or less.

The dielectric layer 150 permits the formation of very high density interconnects. In implementations, such interconnects may be formed using photolithographic techniques. The dielectric layer 150 permits the formation of interconnects having a density of greater than: about 50 input/output connections per millimeter (IO/mm); about 75 IO/mm; about 100 IO/mm; about 125 IO/mm; or about 150 IO/mm. The use of a resin having a relatively low dielectric constant in the dielectric layer 150 beneficially reduces the parasitic capacitance losses, particularly in the high frequency applications found in processor-based devices. Additionally, one or more nanofillers may be added to the material used in the dielectric layer 150 to further enhance the performance of the dielectric layer 150. For example, one or more nanofillers may be used to reduce the coefficient of thermal expansion of the dielectric layer 150. In another example, one or more nanofillers may be used to improve the resistance of the dielectric layer 150 to electromigration.

The pendant groups 160 may include any chemical moiety capable of bonding with a noble metal (e.g., copper) via a coordinate covalent bond. As used herein a coordinate covalent bond may be referred to as a dative covalent bond. Regardless of the terminology, a coordinate covalent bond and a dative covalent bond refer to a covalent bond (i.e., a bond in which electrons are shared) in which the electrons forming the covalent bond originate or are sourced from the same atom and are shared by both atoms.

The properties of an illustrative dielectric layer 150 are presented in TABLE 1, below:

TABLE 1

| PROPERTIES OF AN ILLUSTRATIVE DIELECTRIC MATERIAL | | |
|---|---|---|
| Property | Condition | Target |
| Dielectric Constant (Dk) | 10 GHz | <3.0 |
| Peel Strength to roughened Cu - kgf/cm | | >0.8 |
| Peel Strength to electroless Cu - kgf/cm | | >0.8 |
| Loss Tangent | 10 GHz | <0.001 |
| Surface Roughness after Desmear (Rq) - nm | | <200 |
| Coefficient of Thermal Expansion ($CTE_{25-150}$) | 25-150 C. | <10 |
| Coefficient of Thermal Expansion ($CTE_{150-240}$) | 150-240 C. | <30 |
| Young's Modulus - Gpa | 25 C. | >13 |
| Minimum Melting Viscosity in Processing Window - Poise | | <4000 |
| Water Absorption - % | 100 C., 1 hr | <0.5 |

The material used in forming the dielectric layer 150 commences with the cycotrimerization of cyanate ester molecules (1) to form a monomeric triazine species (2) in the presence of a nucleophile.

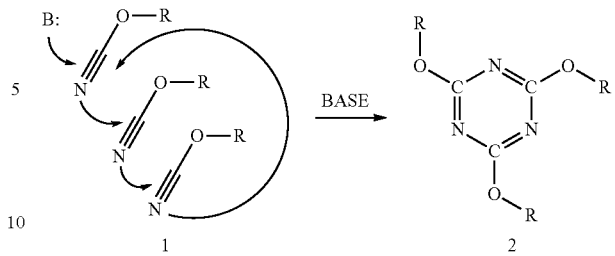

The triazine isomerizes to a substituted triazine (3):

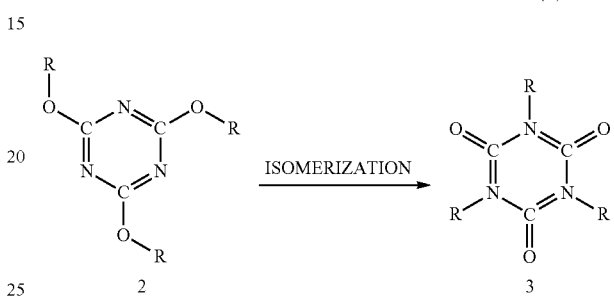

The "R" functional groups in the above three species may be a bisphenol AF-based cyanate ester (4):

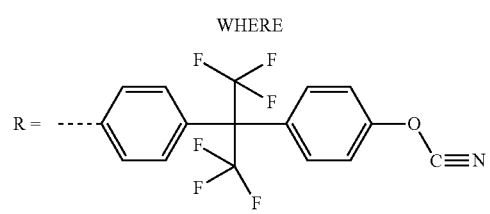

The substituted triazine (3) reacts with epoxy groups, such as those in the bisphenol AF derivative (5) to form bisphenol AF containing an oxazolidine ring (6). In implementations, the dielectric layer 150 may include the bisphenol AF containing the oxazolidine ring (6).

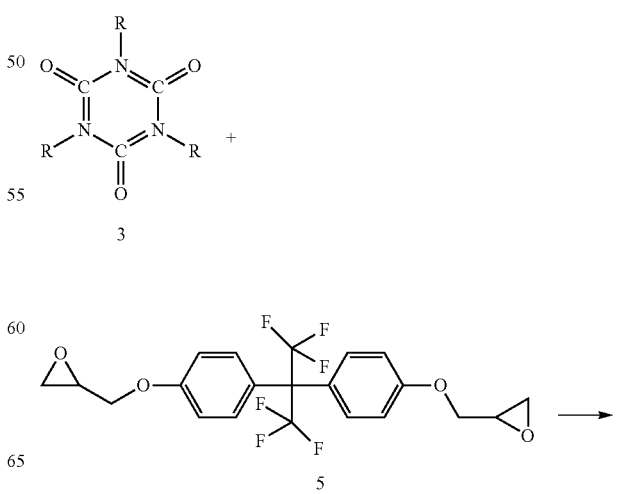

-continued

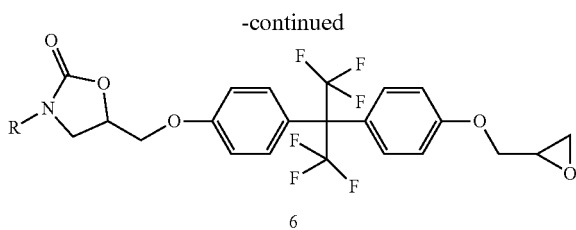

6

The bisphenol AF containing the five member oxazolidine ring (6) beneficially provides a low dielectric constant and loss tangent due, in part, to the presence of the aromatic rings. Furthermore, cyanate ester epoxy reaction beneficially proceeds without the formation of undesirable hydroxyl groups typically found in epoxy-hardener systems. Consequently, the cyanate ester resin systems beneficially exhibit lower moisture absorption and greater chemical resistance than epoxy-hardener systems. Furthermore, the R functional groups on the triazine moiety (2) may be selected to enhance the electrical properties of the dielectric layer 150. The R functional groups may also be selected to favor the propagation and cross-linking of the dimeric epoxy/cyanate ester molecule to an extended polymeric network (e.g., to form a polycyanurate (7)), thereby further enhancing the mechanical stability of the dielectric layer 150.

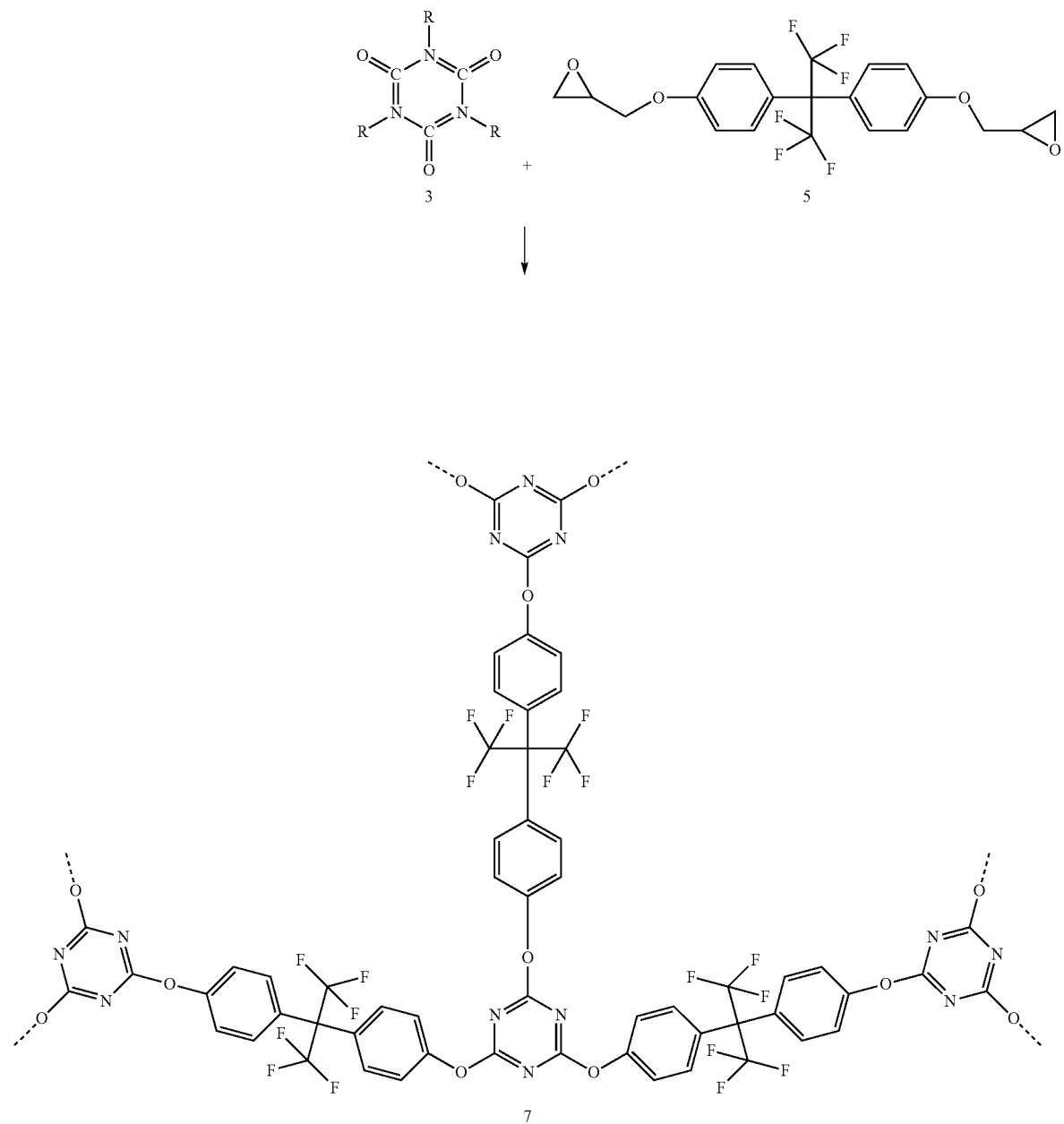

Additionally, the pendant epoxy group on the bisphenol AF moiety (6) reacts with a thiol-terminated polyimide species (8).

porate mercaptoamine (10) or dithiol (11), both of which react with epoxy groups within the resin, into the dielectric layer.

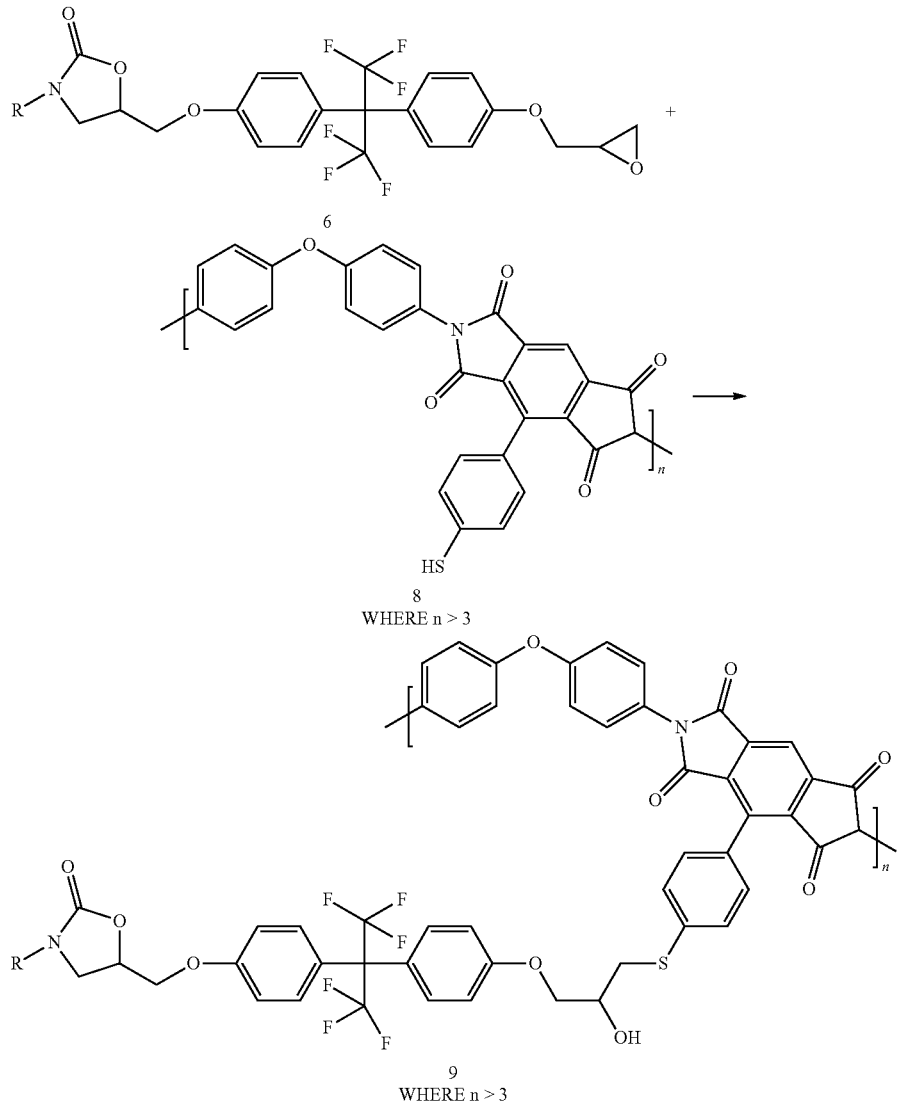

The thiol-terminated functional group of the polyimide (8) crosslinks with the epoxy resin (6) to form the substituted polyimide (9) resin that includes a thioether. In embodiments, the dielectric layer 150 may include the substituted polyimide (9) resin.

In addition to chemically bridging the PI to epoxy interface, the thiol functional group may form coordination complexes with noble metals such as ruthenium (Ru); rhodium (Rh); palladium (Pd); silver (Ag); Osmium (Os); Iridium (Ir); platinum (Pt); gold (Au); and copper (Cu). By controlling the stoichiometry of the varnish or the number of thiol moieties in the polyimide chain, the thiol-polyimide may function as an adhesion promoter to conductive structures 120 formed using one or more noble metals or alloys containing one or more noble metals.

Another method to promote adhesion of the dielectric layer to a noble metal conductive structure 120 is to incor-

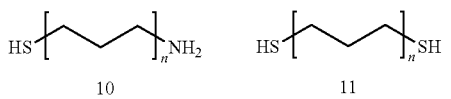

WHERE n FROM 1 TO 20    WHERE n FROM 1 TO 20

Mercaptoamine and dithiol may also be deposited as a surface treatment across all or a portion of the surface of the noble metal conductive structures 120. In embodiments, the mercaptoamine and/or dithiol may be deposited using any currently available or future developed deposition technique, including, but not limited to, electrodeposition, vapor deposition, and/or coating to form a self-assembled monolayer (SAM) of thiol adhesion promoter on the surface of the noble metal conductive structures 120. The dielectric layer 150, used in conjunction with one or more adhesion promoters, beneficially and advantageously minimizes the likelihood of delamination of the dielectric layer 150 from the surface of the conductive structures 120 and also assists in mitigating electromigration through the dielectric layer 150, both of which are advantageous in the application of file line conductive structures 120 and minimizing the spacing between the conductive structures 120.

In embodiments, a polyimide that includes a pendant thiol group (12) may be used as an adhesion promoter between the dielectric layer 150 and the conductive structures 120. In such embodiments, the pendant thiol group bonds to the exposed surface of the conductive structure 120.

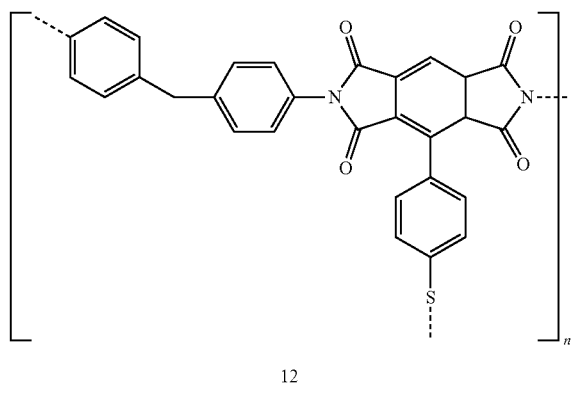

12

WHERE n > 3

In embodiments, the mercaptoamine (10) may be reacted with a polyimide (6) to form an adhesion promoter (13). Such systems and methods minimize the likelihood of delamination of the dielectric layer 150 and/or electromigration within the dielectric layer 150 while enabling fine line spacing ("FLS") down to 2/2 micrometers (μm).

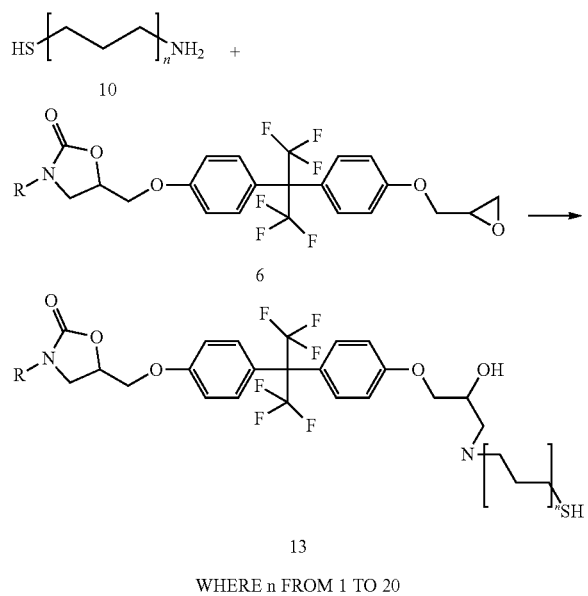

13

WHERE n FROM 1 TO 20

In embodiments, the dithiol (11) may be reacted with a polyimide (1 to form yet another adhesion promoter (14). Such systems and methods minimize the likelihood of delamination of the dielectric layer 150 and/or electromi-gration within the dielectric layer 150 while enabling fine line spacing ("FLS") down to 2/2 micrometers (μm).

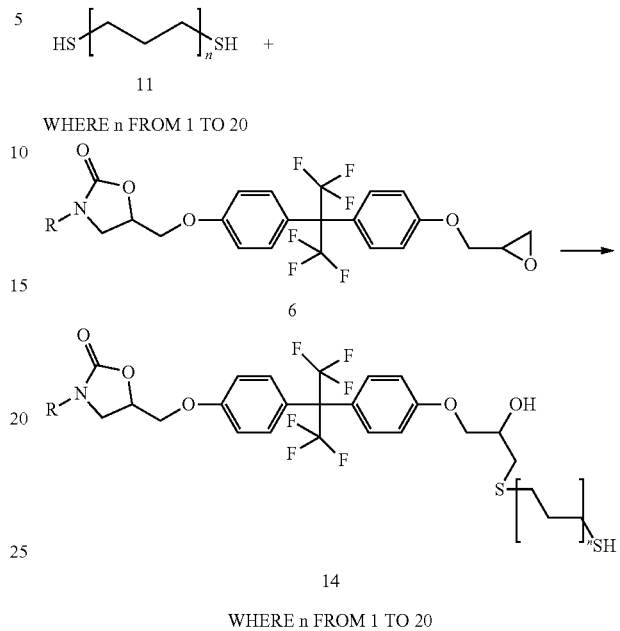

14

WHERE n FROM 1 TO 20

In embodiments, the dielectric layer 150 may include or incorporate one or more fillers or filler materials to reduce the coefficient of thermal expansion ("CTE") of the low dielectric constant resin matrix. In embodiments, such fillers or filler material may enhance the adhesion of the dielectric layer 150 to the conductive structures 120 and/or the first surface of the substrate 110. In embodiments, such fillers or filler material may additionally reduce electromigration within the dielectric layer 150. Non-limiting examples of such fillers include boron nitride (BN) and zirconium tungstate ($Zn(WO_4)_2$). In embodiments, the fillers or filler material may be added as nanoparticles (i.e., particles having a diameter of less than 1 micrometer) to the resin used in the dielectric layer 150. The use of filler nanoparticles enables the patterning of ultra-fine line spacing (e.g., 2 micrometer line width at 2 micrometer spacing, referred to as 2/2).

The properties of both boron nitride and zirconium tungstate are provided in Table 2, below:

TABLE 2

PROPERTIES OF ILLUSTRATIVE FILLERS

| Filler | Dielectric Constant (Dk) | Coefficient of Thermal Expansion (ppm/° C.) |
|---|---|---|
| Boron Nitride (BN) | 4 | 0.1 |
| Zirconium Tungstate ($Zn(WO_4)_2$) | 10 | −8 |

As seen in the above table boron nitride has a relatively low dielectric constant (~4) and a relatively low dissipation factor (~0.001). Boron nitride may be used as the primary filler material in the dielectric layer 150 due to its relatively favorable dielectric loss properties. As an added benefit, boron nitride has a relatively high thermal conductivity (~3 W/m·K), reducing the likelihood of thermal stress within the dielectric layer 150. Reducing thermal stresses within the dielectric layer 150 reduces the likelihood of stress cracking within the dielectric layer 150, thereby reducing the tendency for electromigration within the dielectric layer 150.

Zirconium tungstate may be used alone or in conjunction with other fillers or filler materials, such as boron nitride. Zirconium tungstate may be used to assist in offsetting the coefficient of thermal expansion of the resin system. While boron nitride offers a relatively low coefficient of thermal expansion depending on crystallinity, zirconium tungstate exhibits a large, isotropic, and negative coefficient of thermal expansion which assists in reducing the overall coefficient of thermal expansion of the dielectric layer.

Both boron nitride and zirconium tungstate offer similar surface treatments based on silane coupling. In embodiments, the surface hydroxyl groups on the filler particles (15), (18) can couple with a silanol group (16) and through a silanation reaction covalently bond to a selected surface treatment.

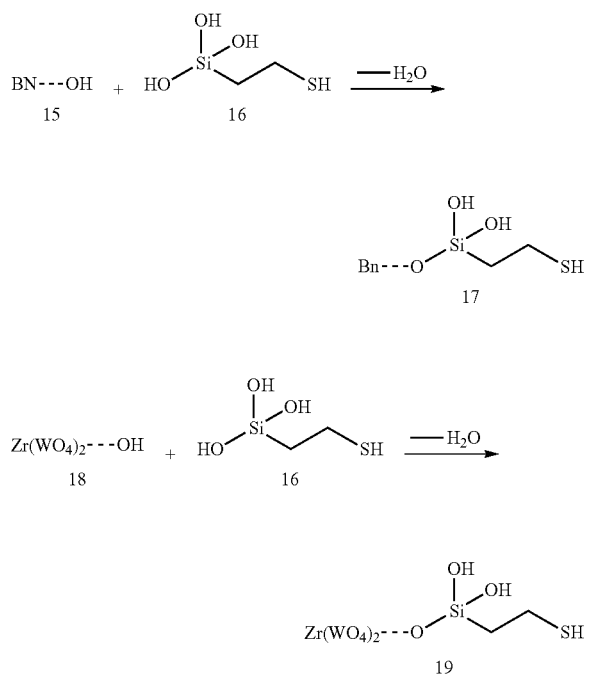

The use of a terminal thiol group enables the filler particle to bind with an epoxy group in the resin or on a noble metal (e.g., copper) surface.

Figure 2:
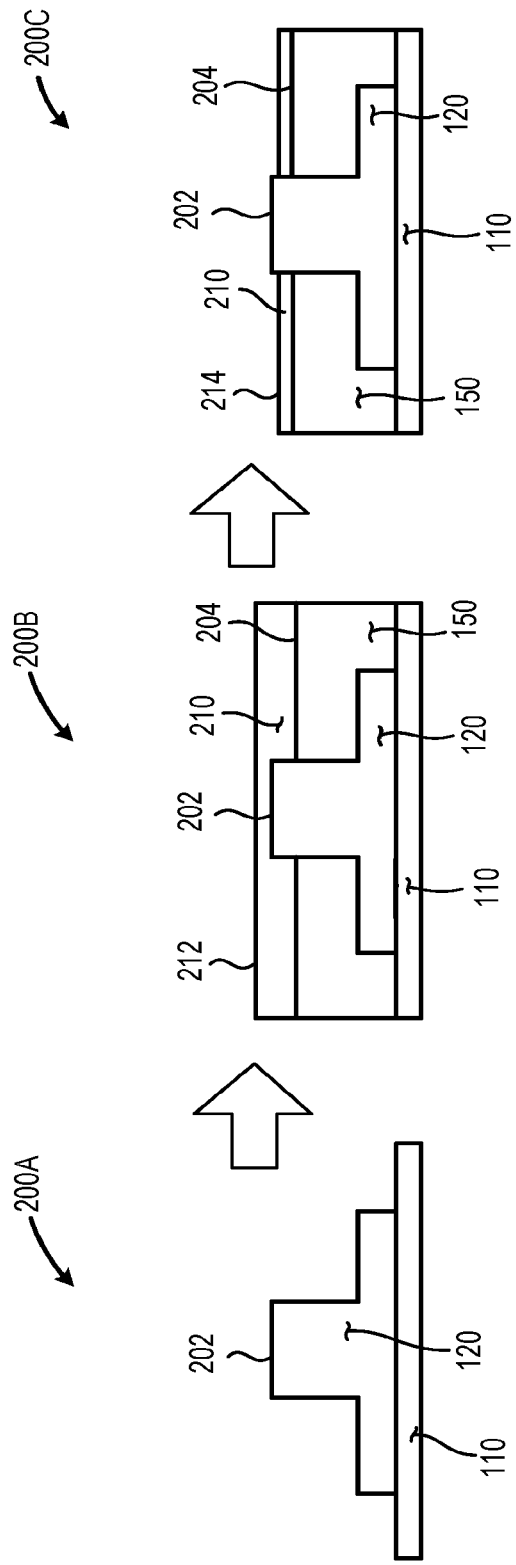
FIG. 2A is a cross sectional elevation of an illustrative system that includes a substrate and a conductive structure, in accordance with at least one embodiment described herein.
FIG. 2B is a cross-sectional elevation of the illustrative system depicted in FIG. 2A with a dielectric layer and a primer layer applied to the dielectric layer and to the conductive structure, in accordance with at least one embodiment described herein.
FIG. 2C is a cross-sectional elevation of the illustrative system depicted in FIG. 2A with a portion of the primer layer removed to expose the conductive structure, in accordance with at least one embodiment described herein.

FIG. 2A is a cross sectional elevation of an illustrative system 200A that includes a substrate 110 and a conductive structure 120, in accordance with at least one embodiment described herein. FIG. 2B is a cross-sectional elevation of the illustrative system depicted in FIG. 2A with a dielectric layer 150 and a primer layer 210 applied to the dielectric layer 150 and to the conductive structure 120, in accordance with at least one embodiment described herein. FIG. 2C is a cross-sectional elevation of the illustrative system depicted in FIG. 2A with a portion of the primer layer 210 removed to expose the conductive structure 120, in accordance with at least one embodiment described herein.

As depicted in FIG. 2A, a system 200A may include one or more conductive structures 120 disposed on a first surface 112 of the substrate 110. The conductive structure 120 may have an upper surface 202. The conductive structure 120 may be deposited, placed, patterned, applied, or otherwise disposed on the first surface 112 of the substrate 110 using any currently available or future developed deposition technique. For example, the conductive structure 120 may be photolithographically patterned on the first surface 112 of the substrate 110. In another example, the conductive structure 120 may be printed using a conductive ink on the first surface 112 of the substrate 110.

The conductive structure 120 may include one or more structures formed, manufactured, or assembled using one or more electrically conductive materials. In embodiments, the conductive structure 120 may include one or more noble metals (gold, silver, copper, platinum, etc.) and/or one or more alloys that contain a noble metal. For example, the conductive structure 120 depicted in FIG. 2A may include a copper structure that has been photolithographically patterned onto the first surface 112 of the substrate 110.

As depicted in FIG. 2B, a dielectric layer 150 may be applied to the conductive structure 120 and to the first surface 112 of the substrate 110. The dielectric layer 150 may be sufficiently thin that the upper surface 202 of the conductive structure 120 remains exposed and projects through the exposed surface 204 of the dielectric layer 150. In implementations, the dielectric layer 150 may covalently bond to at least the conductive structure 120. In implementations, the dielectric layer 150 may covalently bond to the first surface 112 of the substrate 110. In some implementations, one or more bonding agents or adhesion enhancers, such as boron nitride or zirconium tungstate bonded to a terminal thiol group may be disposed across all or a portion of the conductive structure 120, the substrate 110, or both the substrate 110 and the conductive structure 120 prior to the deposition of the dielectric layer 150.

A primer layer 210 may be deposited across all or a portion of the exposed surface 204 of the dielectric layer 150. In embodiments, the primer layer 210 may have sufficient thickness such that the exposed surface 212 of the primer layer 210 covers at least a portion of the upper surface 202 of the conductive structure 120. In embodiments, the primer layer 210 may include a resin carrier such as a polyimide (6):

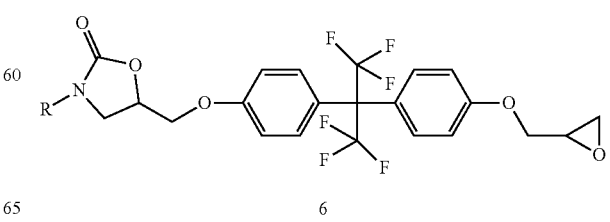

In embodiments, the primer layer 210 may include a resin carrier such as a substituted polyimide (9):

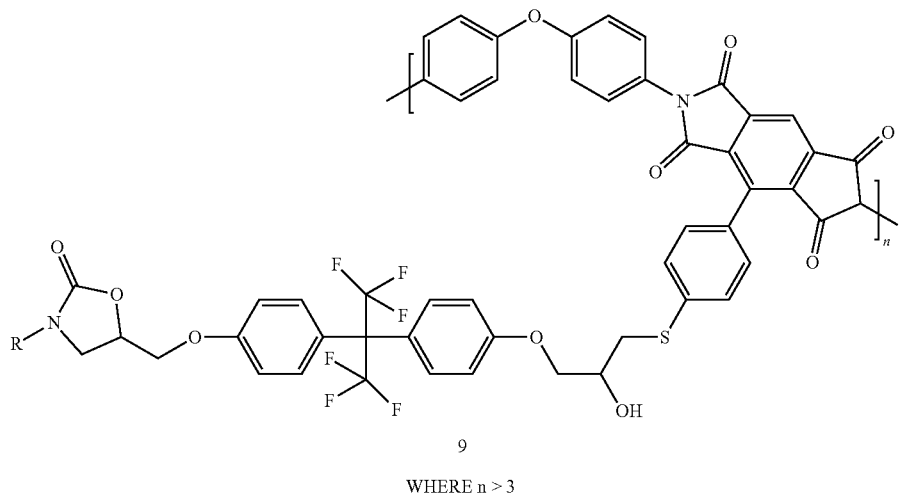

9

WHERE n > 3

In embodiments, the primer layer 210 may include one or more filler materials having desirable electrical or chemical properties. Such filler materials may include, but are not limited to boron nitride (15), zirconium tungstate (18) or combinations thereof:

BN—OH    15

Zr(WO$_4$)$_2$—OH    18

In embodiments where a filler material is employed, the concentration of filler material in the primer layer 210 may be less than or equal to: about 10 weight percent (wt %); about 8 wt %; about 6 wt %; about 4 wt %; about 2 wt %. In embodiments, the primer layer 210 may include a material containing little or no filler material. In embodiments where a filler material is not employed (i.e., the primer layer 210 is "filler free"), the concentration of filler material in the primer layer 210 may be less than or equal to: about 0.3 weight percent (wt %); about 0.2 wt %; about 0.1 wt %; about 0.05 wt %; about 0.01 wt %. The primer layer 210 may be applied using any currently available or future developed deposition or application technique capable of producing a dry primer layer thickness of: about 10 micrometers (μm) or less; about 7 μm or less; about 5 μm or less; about 3 μm or less; or about 7 μm or less.

As depicted in FIG. 2C, a portion of the exposed surface 212 of the primer layer 210 has been removed to expose an intermediate surface 214 of the primer layer 210. In embodiments, the portion of the primer layer 210 removed may expose the upper surface 202 of the conductive structure 120. In some implementations, the upper surface 202 of the conductive structure 120 may project above the intermediate surface 214 of the primer layer 210. In some implementations, the upper surface 202 of the conductive structure 120 may be flush with the intermediate surface 214 of the primer layer 210.

Figure 3:
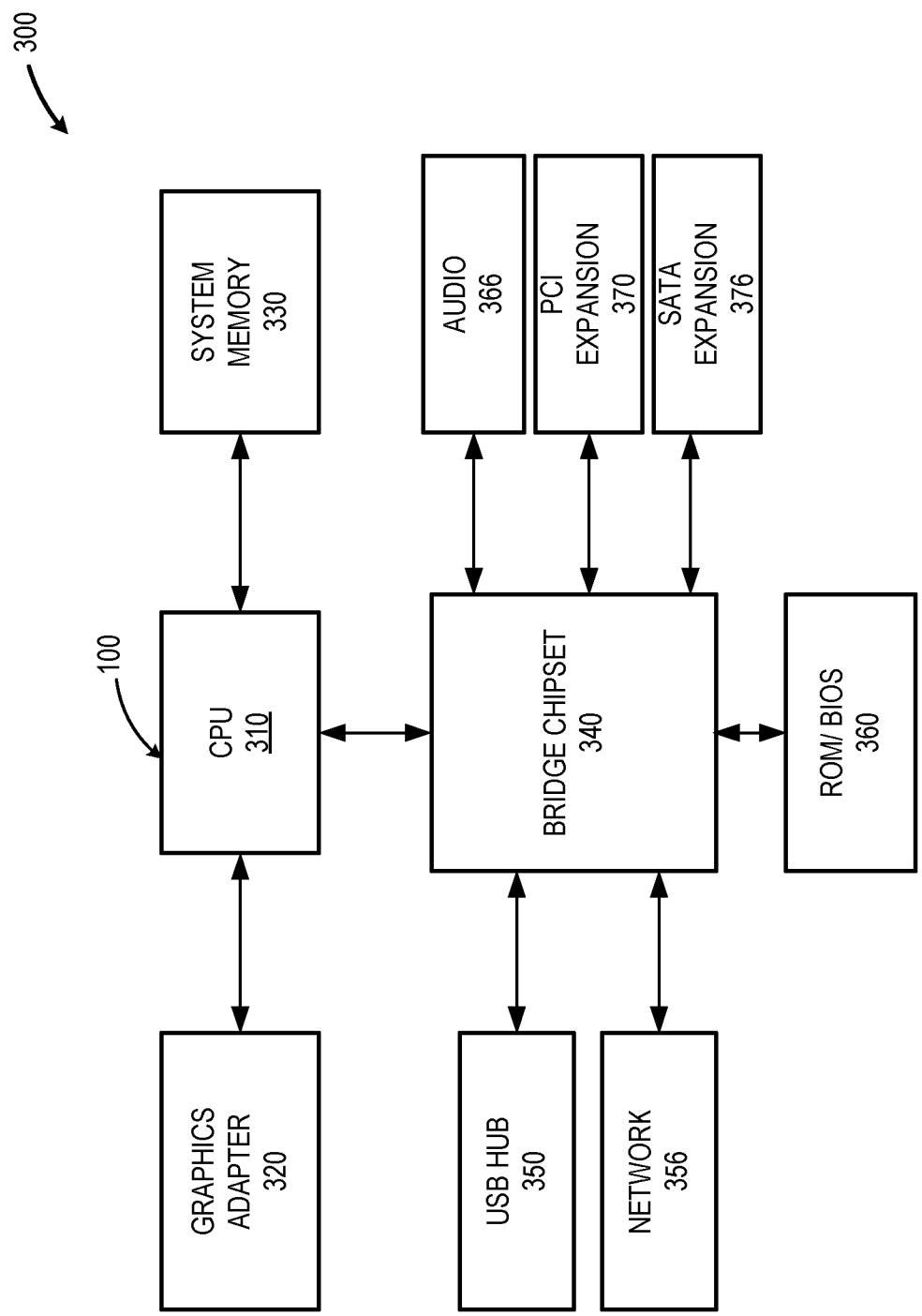
FIG. 3 is a block diagram of an illustrative processor-based system, in accordance with at least one embodiment described herein.

FIG. 3 is a block diagram of an illustrative processor-based system 300 that uses one or more very high density interconnects to a semiconductor substrate 110, in accordance with at least one embodiment described herein. In embodiments, the processor-based device 300 may include a central processing unit (CPU) 310 communicably coupled to a graphics adapter 320, system memory 330, and a bridge chipset 340. In embodiments, at least some of: the CPU 310; the graphics adapter 320; the system memory 330; and/or the bridge chipset 340 may be fabricated, in whole or in part, using a semiconductor substrate 110 containing conductive structures 120 and a dielectric layer 150 such as described in detail in FIGS. 1 and 2. The bridge chipset 340 communicably couples to various external and input/output devices including: a universal serial bus (USB) hub 350, one or more wired or wireless network adapters 356, a read only memory 360 that contains a basic input/output system (BIOS), an audio adapter 366, a peripheral component interconnect (PCI/PCI-e) expansion hub 370, and/or a serial AT attachment (SATA/eSATA) expansion hub 376.

The CPU 310 may include any number of cores, processing units, or similar logical processing units capable of executing one or more machine-executable instruction sets. In embodiments, the CPU 310 may include one or more semiconductor substrates 110 containing conductive structures 120 and a dielectric layer 150 such as depicted and described in FIGS. 1 and 2. The CPU 210 may include any number, type, or combination of devices. At times, the CPU 310 may be implemented in whole or in part in the form of semiconductor devices such as diodes, transistors, inductors, capacitors, and resistors. Such an implementation may include, but is not limited to any current or future developed single- or multi-core processor or microprocessor, such as: on or more systems on a chip (SOCs); central processing units (CPUs); digital signal processors (DSPs); graphics processing units (GPUs); application-specific integrated circuits (ASICs), field programmable gate arrays (FPGAs), and the like. Example processor circuitry may include, but is not limited to, single- and multi-core processors and microprocessors such as: Intel® Pentium® series processors; Intel® Xeon® series coprocessors; Intel® Core® series processors; Intel® Core2® series processors; Intel® Celeron series processors; Apple® A series processors; and similar. Unless described otherwise, the construction and operation of the various blocks shown in FIG. 3 are of conventional design. Consequently, such blocks need not be described in further detail herein, as they will be understood by those skilled in the relevant art. The communications links that communicably couple the blocks depicted in FIG. 3 may include one or more serial and/or parallel buses that employ any known serial or parallel bus structures or architectures.

The processor-based system 300 may include one or more graphics adapters 320 that receive data from one or more system components and convert the data for display on a communicably coupled display device such as a liquid crystal display (LCD) monitor or touchscreen; or a light emitting diode (LED) monitor or touchscreen. The one or more graphics adapters 320 may include one or more graphics processing units (GPUs).

The processor-based system 300 may include system memory 330. The system memory 330 may include any number and/or combination of devices, systems, or combinations thereof suitable for at least the temporary storage of data by the CPU 310. The system memory 330 may include random access memory (RAM), dynamic random access memory (DRAM), programmable read only memory (PROM), erasable programmable read only memory (EPROM), electrically erasable programmable read-only memory (EEPROM), static random access memory (SRAM), double data rate memory (DDR/DDR2/DDR3/DDR4)), or combinations thereof. The system memory 330 may have any storage capacity (2 megabytes (MB), 100 MB, 500 MB, 1 gigabyte (GB), 100 GB, 500 GB, 1 terabyte (TB), 5 TB, 10 TB, 50 TB, etc.).

The system 300 may include one or more bridge chipsets 340 capable of facilitating the exchange of data between the CPU 310 and one or more peripheral devices, networks, hubs, or similar. A non-limiting example of a bridge chipset includes the Intel® Express Chipset as offered by Intel Corp., (SANTA CLARA, Calif.). In some implementations, the bridge chipset 340 may be analogized to a "translator" that receives information and/or data in a first format and converts the information and/or data to a second format. For example, the bridge chipset 340 may receive information and/or data from a network connected device that is in a first format unreadable by the CPU 310. In such an instance, the bridge chipset 340 may translate the information and/or data to a second format compatible with the CPU prior to communicating the information to the CPU 310.

The bridge chipset 340 communicably couples to various external and input/output devices including: a universal serial bus (USB) hub 350, one or more wired or wireless network adapters 356, a read-only memory 360 that contains a basic input/output system (BIOS), an audio adapter 366, a peripheral component interconnect (PCI/PCI-e) expansion hub 370, and/or a serial AT attachment (SATA/eSATA) expansion hub 376.

The USB hub 350 may include any number and/or combination of systems and/or devices capable of bidirectionally communicating information and/or data between one or more external devices (e.g., I/O devices, sensors, network adapters, memory devices) and the bridge chipset 340.

The network adapter 356 may include one or more wired and/or one or more wireless network adapters 356. Example wireless network adapters 256 include, but are not limited to, one or more: IEEE 802.11 (Wi-Fi®) compatible adapters; BLUETOOTH® adapters; near field communication (NFC) adapters; cellular adapters; and similar. Example wired adapters 356 include, but are not limited to, one or more: IEEE 802.3 (Ethernet) adapters.

The read-only memory ("ROM") 360 may include any number and/or combination of non-volatile storage devices capable of storing information and/or data. Such information and/or data may include basic input/output system ("BIOS") data. A portion of the ROM 360 may be used to store or otherwise retain a basic input/output system. The BIOS provides basic functionality to the processor-based system 300, for example by causing the CPU 310 to load one or more machine-readable instruction sets upon initial system power-up or after a soft or hard system reset.

The audio adapter 366 may include any number and/or combination of devices, systems, or combinations thereof capable of generating an audio output perceptible to the system user. In some implementations, the audio adapter 366 may include one or more audio output devices, such as an internal or external loudspeaker system. In some implementations, the audio adapter 366 may include one or more stereo output jacks, RCA jacks, or similar audio output interfaces.

A peripheral component interconnect (PCI/PCI-e) expansion hub 370 may include one or more devices, systems, or components capable of accepting the communicable coupling of one or more internal or external peripheral devices that include a PCI/PCIe interface. A serial AT attachment (SATA/eSATA) expansion hub 376 may include one or more devices, systems, or components capable of accepting the communicable coupling of one or more internal or external peripheral devices that include a SATA/eSATA interface.

Figure 4:
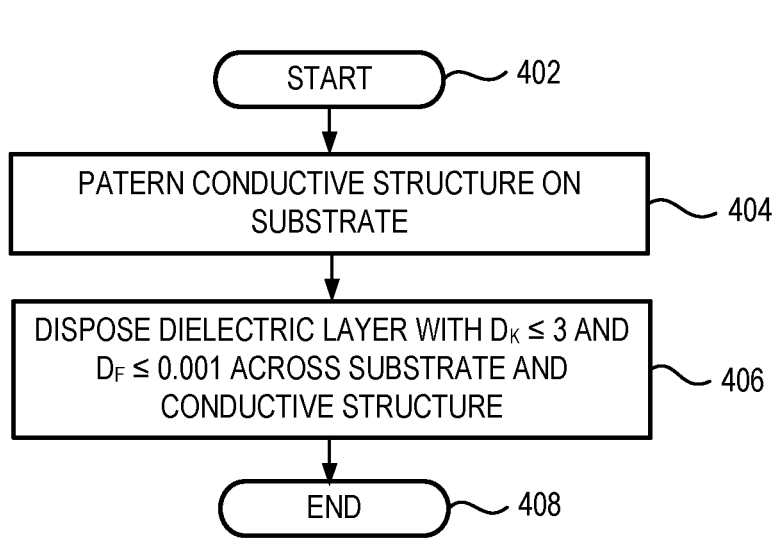
FIG. 4 is a high-level logic flow diagram of an illustrative method of forming a semiconductor substrate that includes at least one conductive structure and a dielectric layer in accordance with the dielectric layer described above in FIGS. 1 and 2, in accordance with at least one embodiment described herein.

FIG. 4 is a high-level logic flow diagram of an illustrative method 400 of forming a semiconductor substrate 110 that includes at least one conductive structure 120 and a dielectric layer 150 in accordance with the dielectric layer described above in FIGS. 1 and 2, in accordance with at least one embodiment described herein. The dielectric layer 150 permits the use of very high density interconnects (e.g., ≥100 IO/mm) with the substrate 110 due to the relatively low dielectric constant (e.g., ≤3) of the dielectric layer 150 and the relatively low dissipation factor (e.g., ≤0.001) of the dielectric layer 150. The method 400 commences at 402.

At 404, one or more conductive structures 120 are deposited, formed, disposed, or otherwise patterned on the first surface 112 of the substrate 110. The one or more conductive structures 120 may include any size, shape, or configuration of electrically conductive structure. In some implementations, the one or more conductive structures 120 may include structures formed using one or more noble metals (gold, silver, copper, platinum, etc.) or noble metal alloys (alloys of gold, silver, copper, platinum, etc.) that are photolithographically patterned on the first surface of the substrate 110. In some implementations, the one or more conductive structures 120 may include structures formed using one or more electrically conductive non-metals, resins, polymers, graphenes, or similar compounds that are deposited or formed on the first surface 112 of the substrate 110. In some instances, the properties of the dielectric layer 150 permit the use of narrow conductive structures 120 (e.g., structures 120 having widths of 2 μm or less) on tight spacing (e.g., spacing of 2 μm or less between structures 120).

At 406, a dielectric layer 150 is disposed across at least some of the conductive structures 120 and across at least a portion of the substrate 110. In embodiments, the dielectric layer 150 may include one or more materials having a dielectric constant of ≤3 and a dissipation factor of ≤0.001. In embodiments, the dielectric layer 150 may include one or more fillers such as boron nitride or zirconium tungstate. In embodiments, the dielectric layer 150 may include one or more fillers such as boron nitride or zirconium tungstate bonded to a terminal thiol group to enhance the adhesion of the dielectric layer 150 to either or both the conductive structures 120 and/or the substrate 110. In one or more embodiments, the dielectric layer 150 may have a thickness of about 3 μm.

In some implementations, the dielectric layer 150 may include one or more solid materials heated to an elevated temperature to soften the dielectric layer 150. The softened dielectric layer 150 may then be deposited across at least some of the conductive structures 120 and across at least a portion of the substrate 110. In some implementations, the dielectric layer 150 may include one or more liquids that are applied across at least some of the conductive structures 120 and across at least a portion of the substrate 110. Such liquids may include dielectric materials that are chemically cured, thermally cured, or photo-cured. The method 400 concludes at 408.

Figure 5:
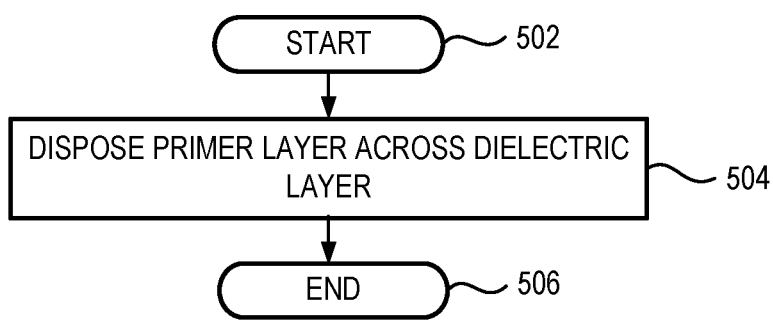
FIG. 5 is a high-level logic flow diagram of an illustrative method of forming a semiconductor substrate that includes at least one conductive structure and a dielectric layer that includes a primer layer such as described above in FIGS. 1 and 2, in accordance with at least one embodiment described herein.

FIG. 5 is a high-level logic flow diagram of an illustrative method 500 of forming a semiconductor substrate 110 that includes at least one conductive structure 120 and a dielectric layer 150 that includes a primer layer 210 such as described above in FIGS. 1 and 2, in accordance with at least one embodiment described herein. The method 500 may be used in conjunction with the method 400 as described in FIG. 4. In some implementations, a primer 210 may be disposed across at least a portion of the dielectric layer 210. The primer layer 210 may also extend across at least a portion of the exposed portions of the conductive structures 120. The method commences at 502.

At 504, a primer layer 210 is disposed on at least a portion of the exposed surface 204 of the dielectric layer 150. In some implementations, the primer layer 210 may be disposed on at least a portion of any conductive structures 120 having exposed surfaces 202 that extend above the dielectric layer 150. In at least one embodiment, the primer layer 210 may have a thickness of about 2 μm. In embodiments, the primer layer 210 may include one or more fillers or similar materials, for example an electrically non-conductive filler at a concentration of from about 1% to about 10% by weight. In embodiments, the primer layer 210 may have a filler content of less than about 0.1% by weight. The method 500 concludes at 506.

Figure 6:
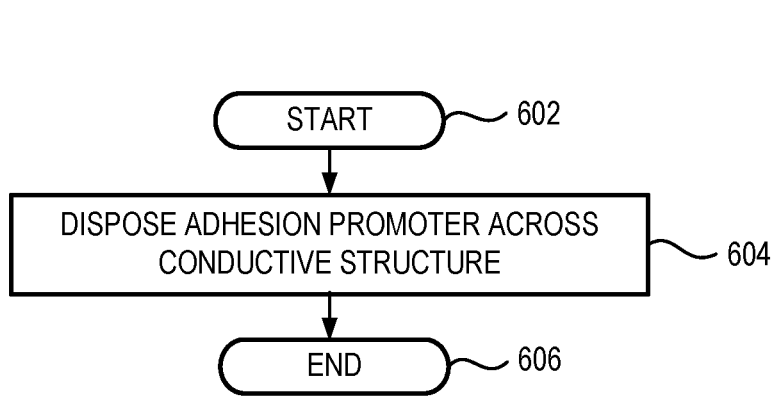
FIG. 6 is a high-level logic flow diagram of an illustrative method of forming a semiconductor substrate that includes at least one conductive structure and a dielectric layer that includes an adhesion promoter disposed across at least a portion of the conductive structures such as described above in FIGS. 1 and 2 and in accordance with at least one embodiment described herein.

FIG. 6 is a high-level logic flow diagram of an illustrative method 600 of forming a semiconductor substrate 110 that includes at least one conductive structure 120 and a dielectric layer 150 that includes an adhesion promoter disposed across at least a portion of the conductive structures 120 such as described above in FIGS. 1 and 2 and in accordance with at least one embodiment described herein. The method 600 may be used in conjunction with the method 400 as described in FIG. 4 and/or the method 500 as described in FIG. 5. In some implementations, an adhesion promoter that improves the bonding of the dielectric layer 150 to the conductive structures 120 and/or the substrate 110 may be disposed across at least some of the conductive structures 120 and/or the substrate 110. The method commences at 602.

At 604, one or more adhesion enhancers, such as mercaptoamine or dithiol that react with the epoxy groups present in the resin used in the dielectric layer 210 may be applied to at least a portion of the conductive structures 120 prior to deposition of the dielectric layer 210. The method 600 concludes at 606.

While FIGS. 4, 5, and 6 illustrate various operations according to one or more embodiments, it is to be understood that not all of the operations depicted in FIGS. 4, 5, and 6 are necessary for other embodiments. Indeed, it is fully contemplated herein that in other embodiments of the present disclosure, the operations depicted in FIGS. 4, 5, and 6, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

As used in this application and in the claims, a list of items joined by the term "and/or" can mean any combination of the listed items. For example, the phrase "A, B and/or C" can mean A; B; C; A and B; A and C; B and C; or A, B and C. As used in this application and in the claims, a list of items joined by the term "at least one of" can mean any combination of the listed terms. For example, the phrases "at least one of A, B or C" can mean A; B; C; A and B; A and C; B and C; or A, B and C.

As used in any embodiment herein, the terms "system" or "module" may refer to, for example, software, firmware and/or circuitry configured to perform any of the aforementioned operations. Software may be embodied as a software package, code, instructions, instruction sets and/or data recorded on non-transitory computer readable storage mediums. Firmware may be embodied as code, instructions or instruction sets and/or data that are hard-coded (e.g., non-volatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry or future computing paradigms including, for example, massive parallelism, analog or quantum computing, hardware embodiments of accelerators such as neural net processors and non-silicon implementations of the above. The circuitry may, collectively or individually, be embodied as circuitry that forms part of a larger system, for example, an integrated circuit (IC), system on-chip (SoC), desktop computers, laptop computers, tablet computers, servers, smartphones, etc.

Any of the operations described herein may be implemented in a system that includes one or more mediums (e.g., non-transitory storage mediums) having stored therein, individually or in combination, instructions that when executed by one or more processors perform the methods. Here, the processor may include, for example, a server CPU, a mobile device CPU, and/or other programmable circuitry. Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), rewritable compact disks (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), embedded multimedia cards (eMMCs), secure digital input/output (SDIO) cards, magnetic or optical cards, or any type of media suitable for storing electronic instructions. Other embodiments may be implemented as software executed by a programmable control device.

Thus, the present disclosure is directed to systems and methods for providing a dielectric layer on a semiconductor substrate capable of supporting very high density interconnects (i.e., ≥100 IO/mm). The dielectric layer includes a maleimide polymer in which a thiol-terminated functional group crosslinks with an epoxy resin. The resultant dielectric material provides a dielectric constant of less than 3 and a dissipation factor of less than 0.001. Additionally, the thiol functional group forms coordination complexes with noble metals present in the conductive structures, thus by controlling the stoichiometry of epoxy to polyimide, the thiol-polyimide may beneficially provide an adhesion enhancer between the dielectric and noble metal conductive structures.

The following examples pertain to further embodiments. The following examples of the present disclosure may comprise subject material such as at least one device, a method, at least one machine-readable medium for storing instructions that when executed cause a machine to perform acts based on the method, means for performing acts based on the method and/or a system for providing dielectric layer compatible with the formation of very high-density interconnects (≥100 IO/mm) on a semiconductor substrate.

According to example 1, there is provided a semiconductor substrate. The semiconductor substrate may include: a substrate having a first surface; at least one conductive structure disposed on at least a portion of the first surface of the substrate; and a dielectric layer disposed across at least a portion of the first surface of the substrate and the at least one conductive structure, the dielectric layer having a dielectric constant (Dk) of less than or equal to 3 and a dissipation factor (Df) of less than or equal to 0.001.

Example 2 may include elements of example 1, where the dielectric layer may include a compound that includes at least one of:

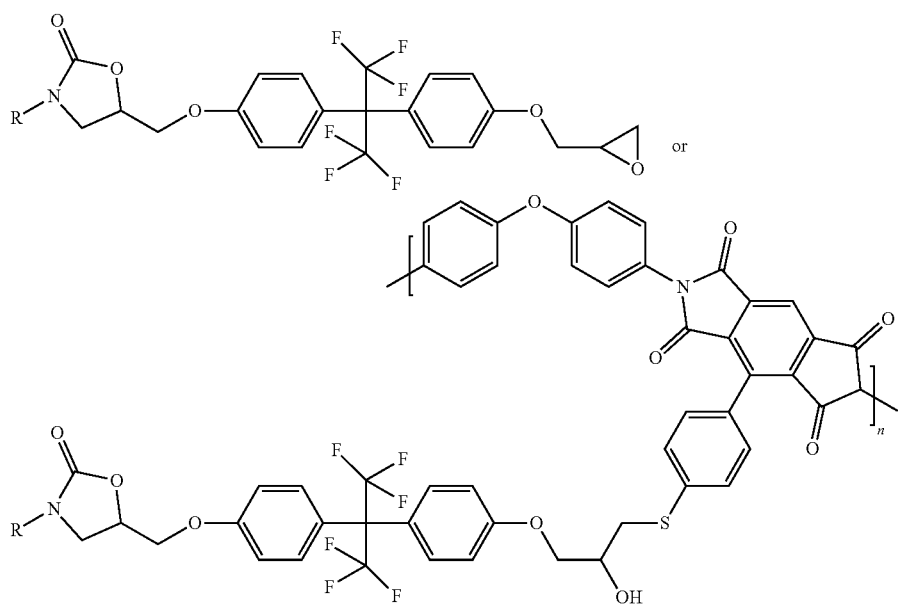

WHERE n > 3

Example 3 may include elements of example 1 where the at least one conductive structure may include at least one copper structure or at least one copper containing alloy structure.

Example 4 may include elements of example 1 where the dielectric layer may further include a filler material that includes one or more of the following: boron nitride (BN) and zirconium tungstate (Zr(WO$_4$)$_2$).

Example 5 may include elements of example 4 where the filler material has a particle size of less than 1 micrometer (μm).

Example 6 may include elements of example 1 where the dielectric layer may additionally include an adhesion promoter that includes at least one of:

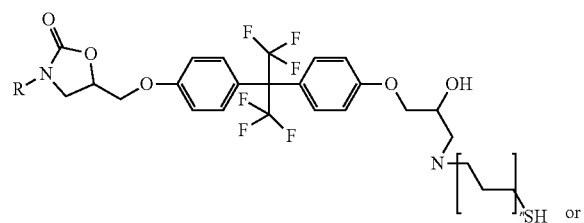

WHERE n FROM 1 TO 20

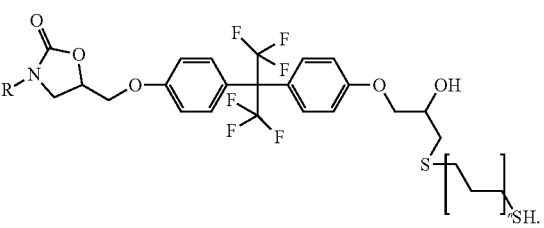

WHERE n FROM 1 TO 20

Example 7 may include elements of example 1 where the dielectric layer may further include an adhesion promoter that includes at least one of:

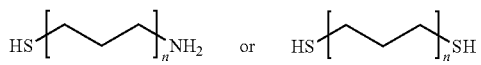

WHERE n FROM 1 TO 20      WHERE n FROM 1 TO 20.

Example 8 may include elements of example 1 where the dielectric layer may further include an adhesion promoter that includes:

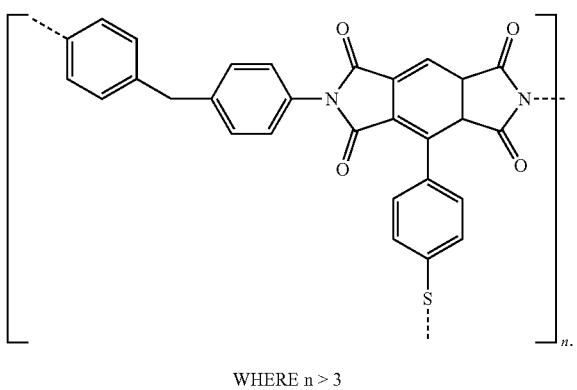

WHERE n > 3

Example 9 may include elements of example 1, and the substrate may additionally include a primer layer disposed across at least a portion of the dielectric layer.

Example 10 may include elements of example 9 where the primer layer may include a primer that includes one or more of the following:

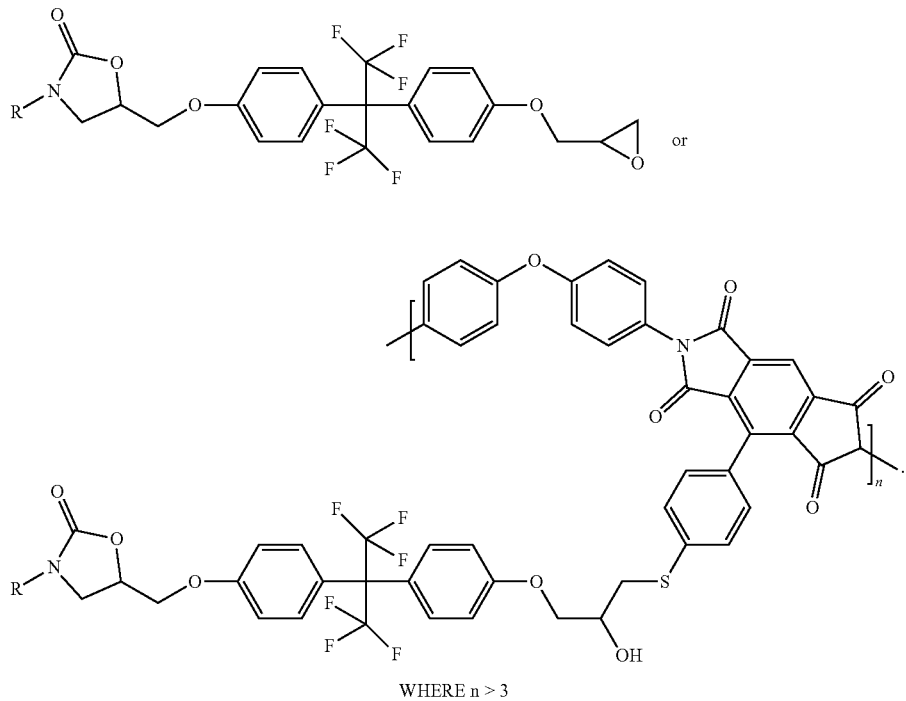

WHERE n > 3

Example 11 may include elements of example 10 where the primer may include a filler content of less than about 0.1 percent by weight (wt %).

Example 12 may include elements of example 10 where the primer may include a filler having a concentration of less than about 10 percent by weight (wt %).

Example 13 may include elements of example 12 where the primer may include a filler that includes at least one of:

BN—OH or Zr(WO$_4$)$_2$—OH.

Example 14 may include elements of any of examples 1 through 9 and the substrate may additionally include an adhesion promoter disposed at least partially across the surface of the at least one conductive structure.

Example 15 may include elements of example 14 where the adhesion promoter may include a mercaptosilane derivative having a terminating thiol functional group selected from the following:

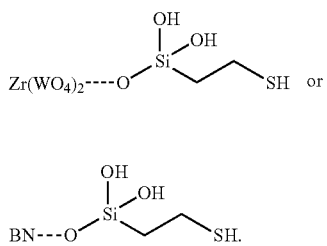

According to example 16, there is provided a method of fabricating a semiconductor substrate. The method may include: patterning at least one conductive structure on a first surface of a substrate; and disposing a dielectric layer having a dielectric constant (Dk) of less than or equal to 3 and a dissipation factor (DO of less than or equal to 0.001 across at least a portion of the substrate and the at least one conductive structure.

Example 17 may include elements of example 16 where disposing a dielectric layer across at least a portion of the substrate and the at least one conductive structure may include disposing, across at least a portion of the substrate and at least a portion of the at least one conductive structure, a dielectric layer comprising a compound that includes at least one of:

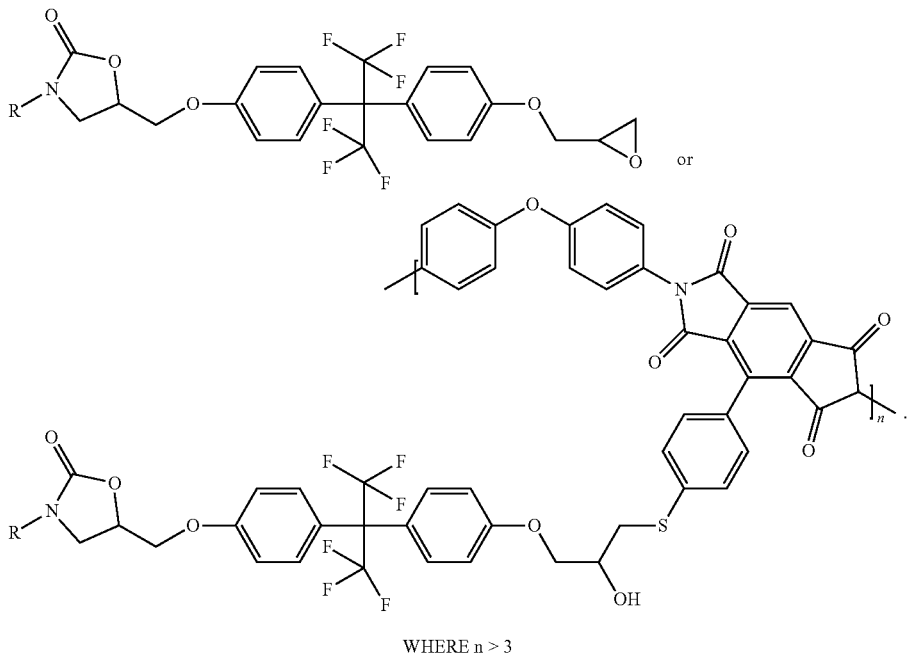

WHERE n > 3

Example 18 may include elements of example 16 where disposing a dielectric layer across at least a portion of the substrate and the at least one conductive structure may include disposing a dielectric layer across at least a portion of the substrate and at least a portion of at least one copper structure.

Example 19 may include elements of example 16 where disposing a dielectric layer across at least a portion of the substrate and the at least one conductive structure may include disposing, across at least a portion of the substrate and at least a portion of the at least one conductive structure, a dielectric layer comprising a compound that includes one or more of the following: boron nitride (BN) and zirconium tungstate (Zr(WO$_4$)$_2$).

Example 20 may include elements of example 19 where disposing a dielectric layer across at least a portion of the substrate and the at least one conductive structure may include disposing, across at least a portion of the substrate and at least a portion of the at least one conductive structure, a dielectric layer comprising a filler material having a particle size of less than 1 micrometer (μm).

Example 21 may include elements of example 16 where disposing a dielectric layer across at least a portion of the substrate and the at least one conductive structure may include disposing, across at least a portion of the substrate and at least a portion of the at least one conductive structure, a dielectric layer comprising an adhesion promoter that includes at least one of:

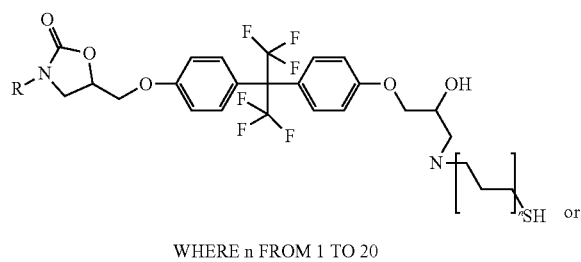

WHERE n FROM 1 TO 20

-continued

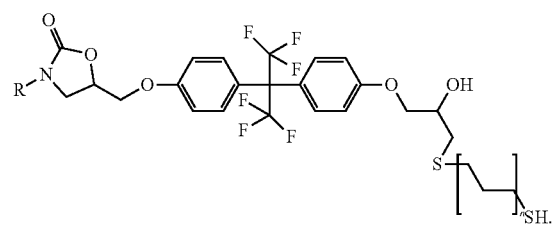

WHERE n FROM 1 TO 20

Example 22 may include elements of example 16 where disposing a dielectric layer across at least a portion of the substrate and the at least one conductive structure may include disposing, across at least a portion of the substrate and at least a portion of the at least one conductive structure, a dielectric layer comprising an adhesion promoter that includes at least one of:

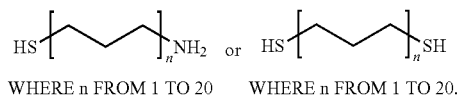

WHERE n FROM 1 TO 20    WHERE n FROM 1 TO 20.

Example 23 may include elements of example 16 where disposing a dielectric layer across at least a portion of the substrate and the at least one conductive structure may include disposing, across at least a portion of the substrate and at least a portion of the at least one conductive structure, a dielectric layer comprising an adhesion promoter that includes:

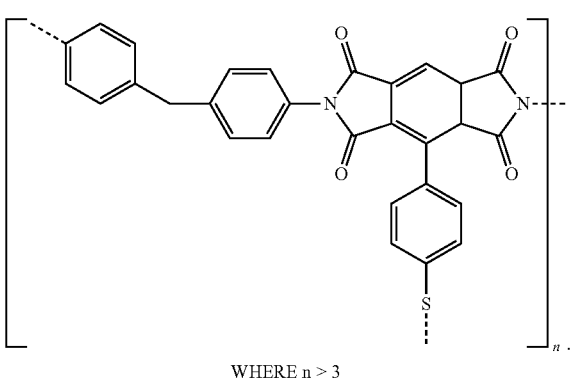

WHERE n > 3

Example 24 may include elements of example 16, and the method may additionally include disposing a primer layer across at least a portion of the dielectric layer.

Example 25 may include elements of example 24 where disposing a primer layer across at least a portion of the dielectric layer may include disposing, across at least a portion of the dielectric layer, a primer layer that includes a primer at least one of:

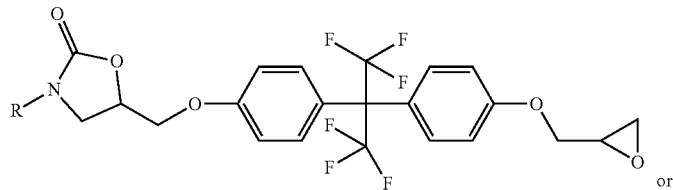

or

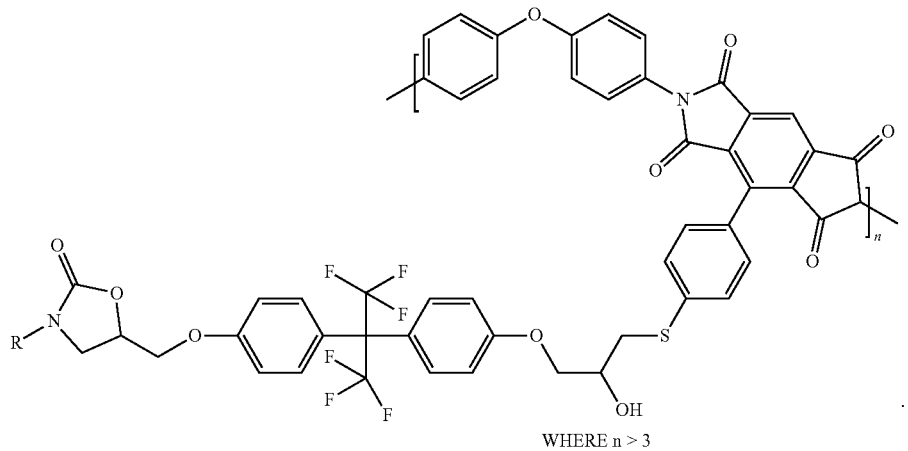

WHERE n > 3

Example 26 may include elements of example 25 where disposing a primer layer across at least a portion of the dielectric layer may include disposing, across at least a portion of the dielectric layer, a primer that includes a filler that includes at least one of:

BN—OH or Zr(WO$_4$)$_2$—OH.

Example 27 may include elements of example 26 where disposing a primer layer across at least a portion of the dielectric layer may include disposing, across at least a portion of the dielectric layer, a primer layer having a filler content of less than 0.1 percent by weight (wt %).

Example 28 may include elements of example 26 where disposing a primer layer across at least a portion of the dielectric layer comprises disposing, across at least a portion of the dielectric layer, a primer layer that includes a filler having a concentration of from about 1 percent by weight (wt %) to about 10 wt %.

Example 29 may include elements of any of examples 16 through 28, and the method may additionally include disposing an adhesion promoter at least partially across the surface of the at least one conductive structure.

Example 30 may include elements of example 29 where disposing an adhesion promoter at least partially across the surface of the at least one conductive structure may include disposing, at least partially across the surface of the at least one conductive structure an adhesion promoter that includes a mercaptosilane derivative having a terminating thiol functional group selected from the following:

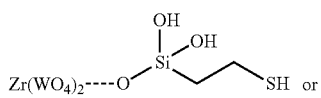

-continued

BN---O-Si(OH)(OH)-CH$_2$CH$_2$-SH.

According to example 31, there is provided a dielectric material having a dielectric constant (Dk) of less than or equal to 3 and a dissipation factor (Df) of less than or equal to 0.001 and comprising a compound that includes at least one of:

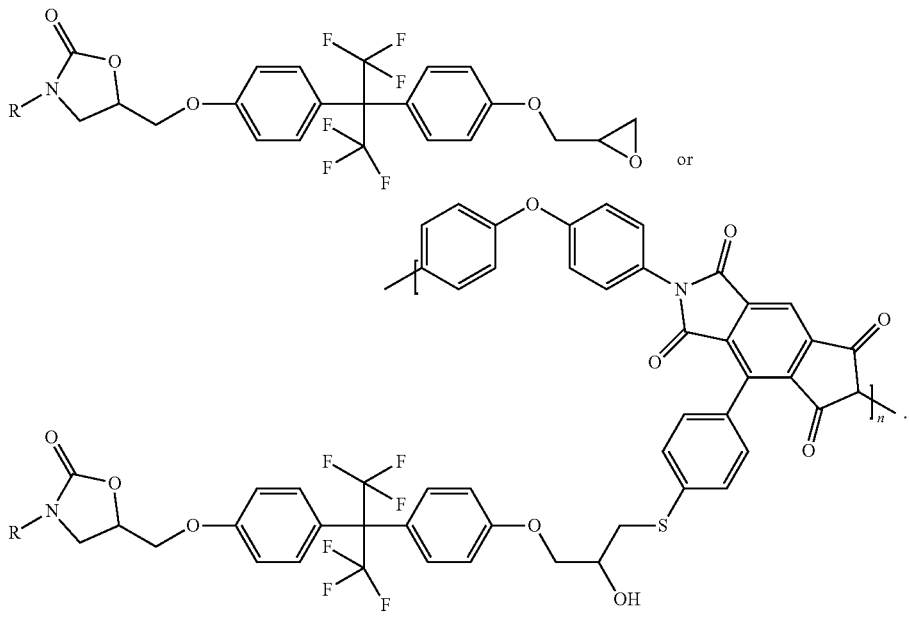

Example 32 may include elements of example 31, and the dielectric material may additionally include a filler material that includes one or more of the following: boron nitride (BN) and zirconium tungstate ($Zr(WO_4)_2$).

Example 33 may include elements of example 32 where the filler material has a particle size of less than 1 micrometer (μm).

Example 34 may include elements of example 31, and the dielectric material may additionally include an adhesion promoter that includes at least one of:

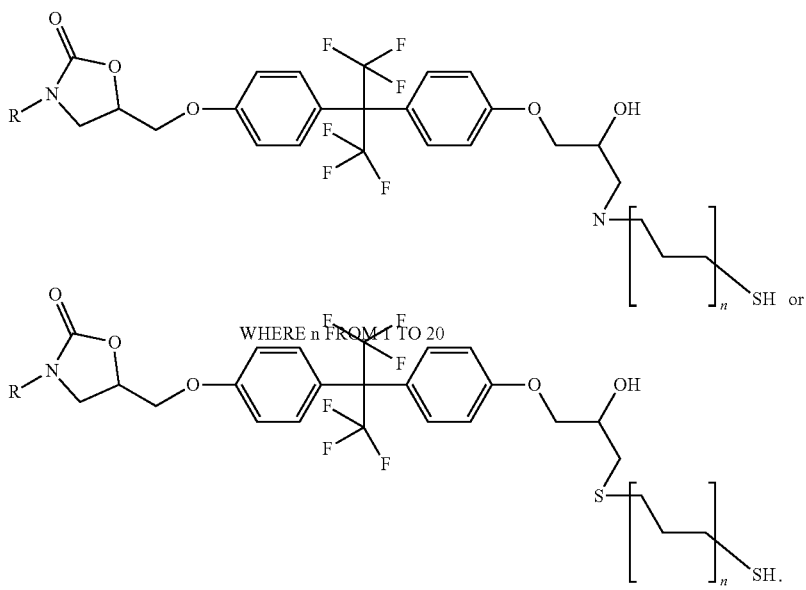

Example 35 may include elements of example 31, and the dielectric material may additionally include an adhesion promoter that includes at least one of:

WHERE n FROM 1 TO 20    WHERE n FROM 1 TO 20

Example 36 may include elements of example 31, and the dielectric material may additionally include an adhesion promoter that includes:

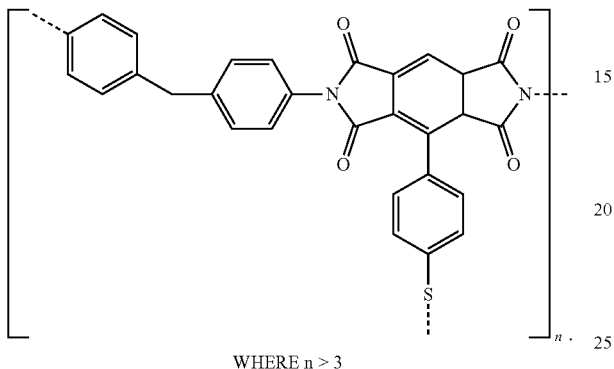

WHERE n > 3

According to example 37, there is provided a system that includes at least one high density interconnect between a semiconductor package and a substrate, the substrate comprising: a first surface; at least one conductive structure disposed on at least a portion of the first surface of the substrate; a dielectric layer disposed across at least a portion of the first surface of the substrate and the at least one conductive structure, the dielectric layer having a dielectric constant (Dk) of less than or equal to 3 and a dissipation factor (Df) of less than or equal to 0.001.

Example 38 may include elements of example 37 where the dielectric layer comprises a compound that includes at least one of:

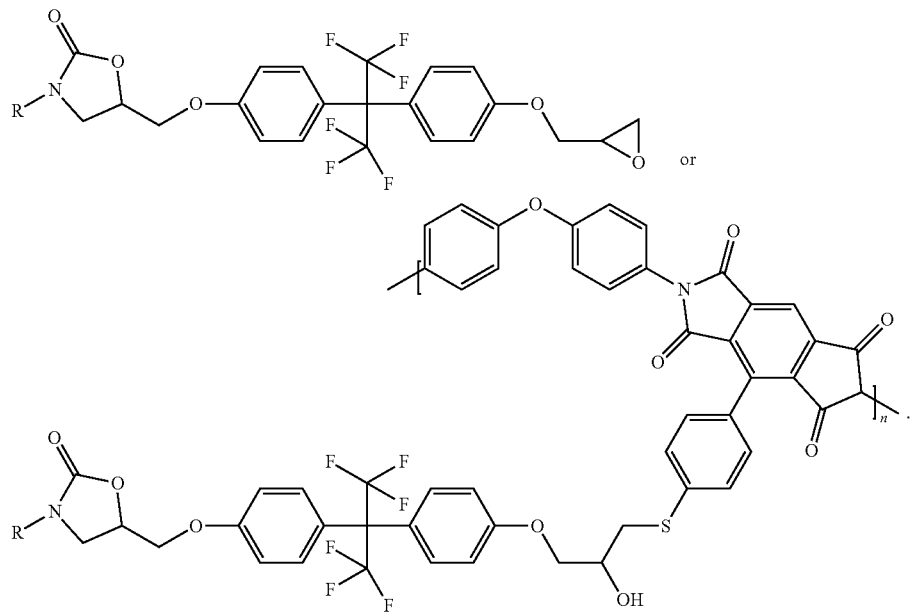

WHERE n FROM 1 TO 20

Example 39 may include elements of example 37 where the at least one conductive structure comprises at least one copper structure or at least one copper containing alloy structure.

Example 40 may include elements of example 37 where the dielectric layer further comprises a filler material that includes one or more of the following: boron nitride (BN) and zirconium tungstate ($Zr(WO_4)_2$).

Example 41 may include elements of example 40 where the filler material has a particle size of less than 1 micrometer (μm).

Example 42 may include elements of example 37 where the dielectric layer further comprises an adhesion promoter that includes at least one of:

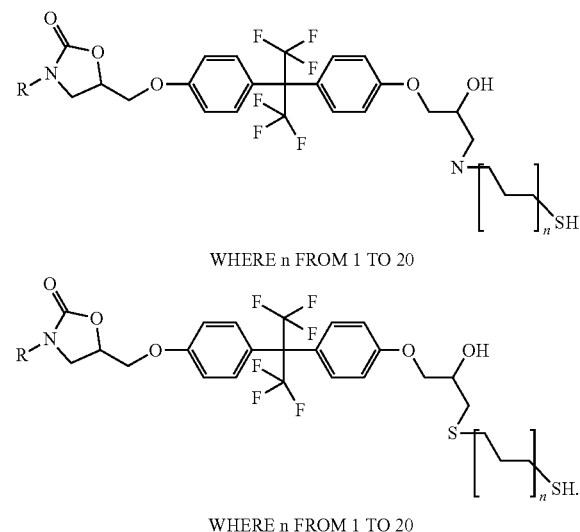

WHERE n FROM 1 TO 20

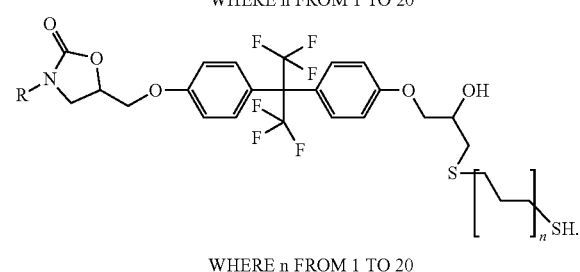

WHERE n FROM 1 TO 20

Example 43 may include elements of example 37 where the dielectric layer may further include an adhesion promoter that includes at least one of:

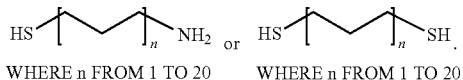

WHERE n FROM 1 TO 20        WHERE n FROM 1 TO 20

Example 44 may include elements of example 37 where the dielectric layer may further include an adhesion promoter that may include:

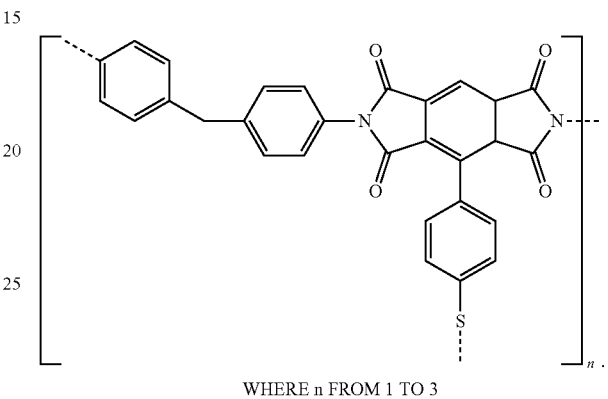

WHERE n FROM 1 TO 3

Example 45 may include elements of example 37 and the system may further include a primer layer disposed across at least a portion of the dielectric layer.

Example 46 may include elements of example 45 where the primer layer comprises a primer that includes one or more of the following:

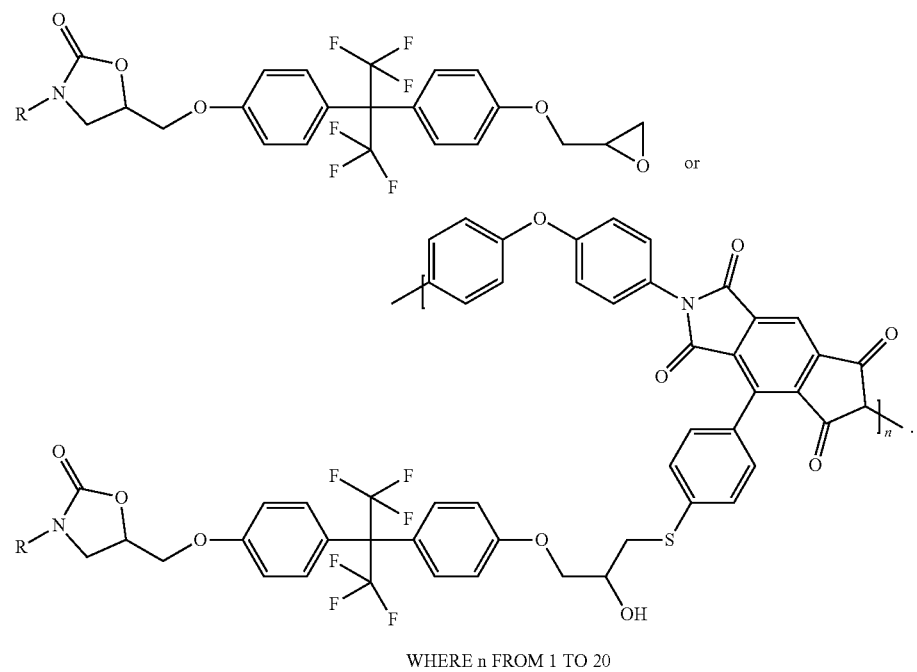

WHERE n FROM 1 TO 20

Example 47 may include elements of example 46 where the primer layer may include a filler that includes at least one of:

BN—OH or Zr(WO$_4$)$_2$—OH.

Example 48 may include elements of example 47 where the primer layer may include a primer having a filler content of less than 0.5% by weight.

Example 49 may include elements of example 47 where the primer layer may include a primer having a filler content of from about 1% by weight (wt %) to about 10 wt %.

Example 50 may include elements of any of example 37 through 45 and the system may additionally include an adhesion promoter disposed at least partially across the surface of the at least one conductive structure.

Example 51 may include elements of example 50 where the adhesion promoter comprises a mercaptosilane derivative having a terminating thiol functional group selected from the following:

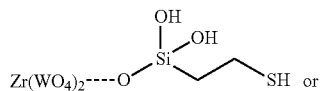

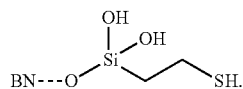

Example 52 may include elements of example 37 where the at least one high density interconnect comprises an interconnect having greater than 50 input/output connections per inch.

Example 53 may include elements of example 37 where the at least one high density interconnect comprises an interconnect having greater than 100 input/output connections per inch.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A semiconductor substrate, comprising:
   a substrate having a first surface;
   at least one conductive structure disposed on at least a portion of the first surface of the substrate;
   a dielectric layer disposed across at least a portion of the first surface of the substrate and the at least one conductive structure, the dielectric layer having a dielectric constant (Dk) of less than or equal to 3 and a dissipation factor (Df) of less than or equal to 0.001.

2. The substrate of claim 1 wherein the dielectric layer comprises a compound that includes at least one of:

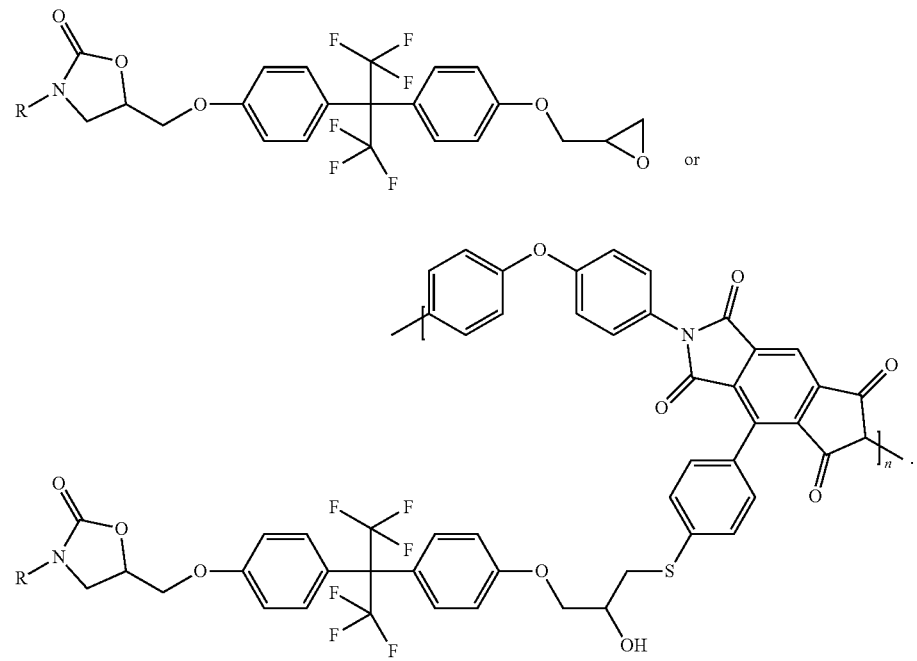

WHERE n FROM 1 TO 20

3. The substrate of claim 1 wherein the at least one conductive structure comprises at least one copper structure or at least one copper-containing alloy structure.

4. The substrate of claim 1 wherein the dielectric layer further comprises a filler material that includes one or more of the following: boron nitride (BN) and zirconium tungstate (Zr(WO$_4$)$_2$).

5. The substrate of claim 4 wherein the filler material has a particle size of less than 1 micrometer (μm).

6. The substrate of claim 1 wherein the dielectric layer further comprises an adhesion promoter that includes at least one of:

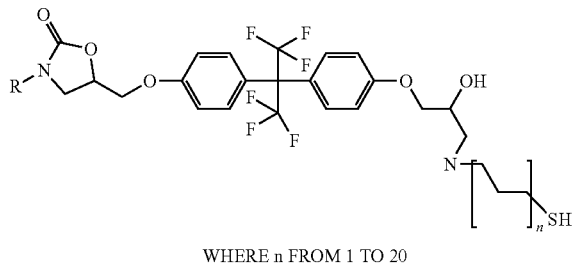

WHERE n FROM 1 TO 20

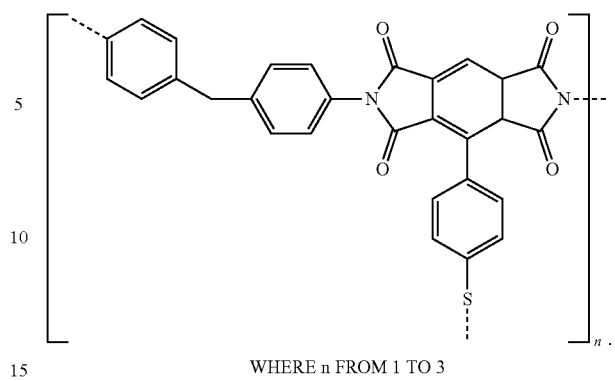

WHERE n FROM 1 TO 3

9. The substrate of claim 1, further comprising a primer layer disposed across at least a portion of the dielectric layer.

10. The substrate of claim 1, further comprising an adhesion promoter disposed at least partially across the surface of the at least one conductive structure.

11. The substrate of claim 10 wherein the adhesion promoter comprises a mercaptosilane derivative having a terminating thiol functional group selected from the following:

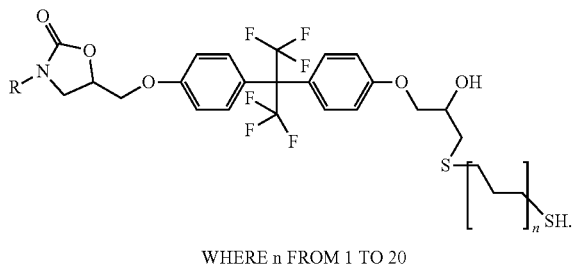

WHERE n FROM 1 TO 20

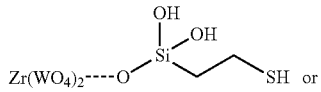

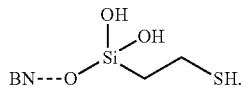

12. A method of fabricating a semiconductor substrate, comprising:
 patterning at least one conductive structure on a first surface of a substrate; and
 disposing a dielectric layer having a dielectric constant (Dk) of less than or equal to 3 and a dissipation factor (Df) of less than or equal to 0.001 across at least a portion of the substrate and across at least a portion of the at least one conductive structure.

13. The method of claim 12 wherein disposing a dielectric layer across at least a portion of the substrate and the at least one conductive structure comprises disposing, across at least a portion of the substrate and at least a portion of the at least one conductive structure, a dielectric layer comprising a compound that includes at least one of:

7. The substrate of claim 1 wherein the dielectric layer further comprises an adhesion promoter that includes at least one of:

 or 

WHERE n FROM 1 TO 20     WHERE n FROM 1 TO 20

8. The substrate of claim 1 wherein the dielectric layer further comprises an adhesion promoter that includes:

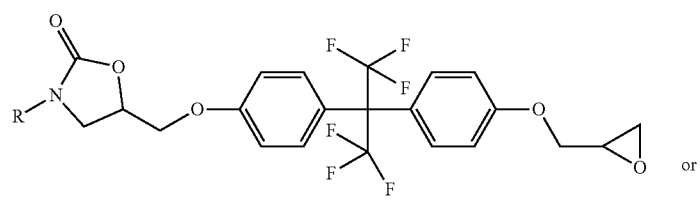 or

-continued

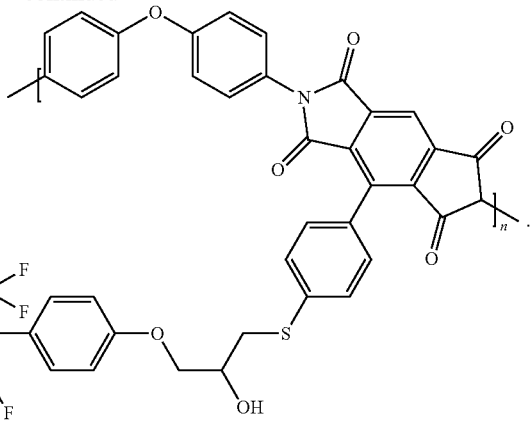

WHERE n FROM 1 TO 20

14. The method of claim 12 wherein disposing a dielectric layer across at least a portion of the substrate and the at least one conductive structure comprises disposing a dielectric layer across at least a portion of the substrate and at least a portion of at least one copper structure.

15. The method of claim 12 wherein disposing a dielectric layer across at least a portion of the substrate and the at least one conductive structure comprises disposing, across at least a portion of the substrate and at least a portion of the at least one conductive structure, a dielectric layer comprising a compound that includes one or more of the following: boron nitride (BN) and zirconium tungstate ($Zr(WO_4)_2$).

16. The method of claim 15 wherein disposing a dielectric layer across at least a portion of the substrate and the at least one conductive structure comprises disposing, across at least a portion of the substrate and at least a portion of the at least one conductive structure, a dielectric layer comprising a filler material having a particle size of less than 1 micrometer ($\mu m$).

17. The method of claim 12 wherein disposing a dielectric layer across at least a portion of the substrate and the at least one conductive structure comprises disposing, across at least a portion of the substrate and at least a portion of the at least one conductive structure, a dielectric layer comprising an adhesion promoter that includes at least one of:

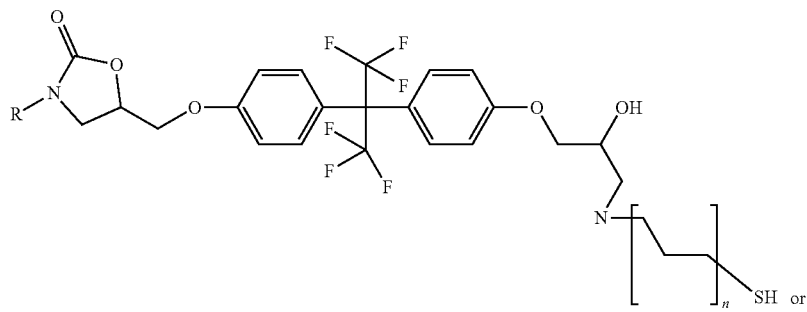

WHERE n FROM 1 TO 20

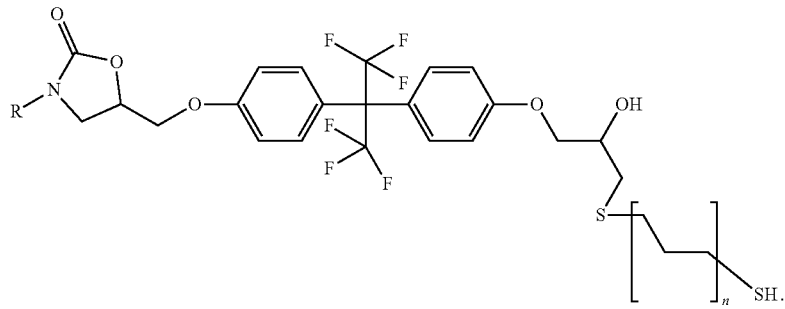

WHERE n FROM 1 TO 20

18. The method of claim 12 wherein disposing a dielectric layer across at least a portion of the substrate and the at least one conductive structure comprises disposing, across at least a portion of the substrate and at least a portion of the at least one conductive structure, a dielectric layer comprising an adhesion promoter that includes at least one of:

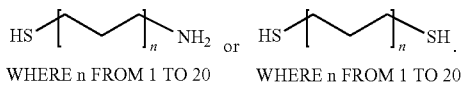

19. The method of claim 12 wherein disposing a dielectric layer across at least a portion of the substrate and the at least one conductive structure comprises disposing, across at least a portion of the substrate and at least a portion of the at least one conductive structure, a dielectric layer comprising an adhesion promoter that includes:

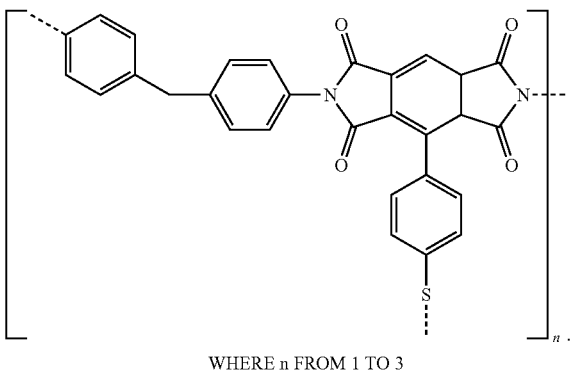

20. The method of claim 12, further comprising:
disposing a primer layer across at least a portion of the dielectric layer.

21. A system that includes at least one high density interconnect between a semiconductor package and a substrate, the substrate comprising:
a first surface;
at least one conductive structure disposed on at least a portion of the first surface of the substrate;
a dielectric layer disposed across at least a portion of the first surface of the substrate and the at least one conductive structure, the dielectric layer having a dielectric constant (Dk) of less than or equal to 3 and a dissipation factor (Df) of less than or equal to 0.001.

22. The system of claim 21 wherein the dielectric layer comprises a compound that includes at least one of:

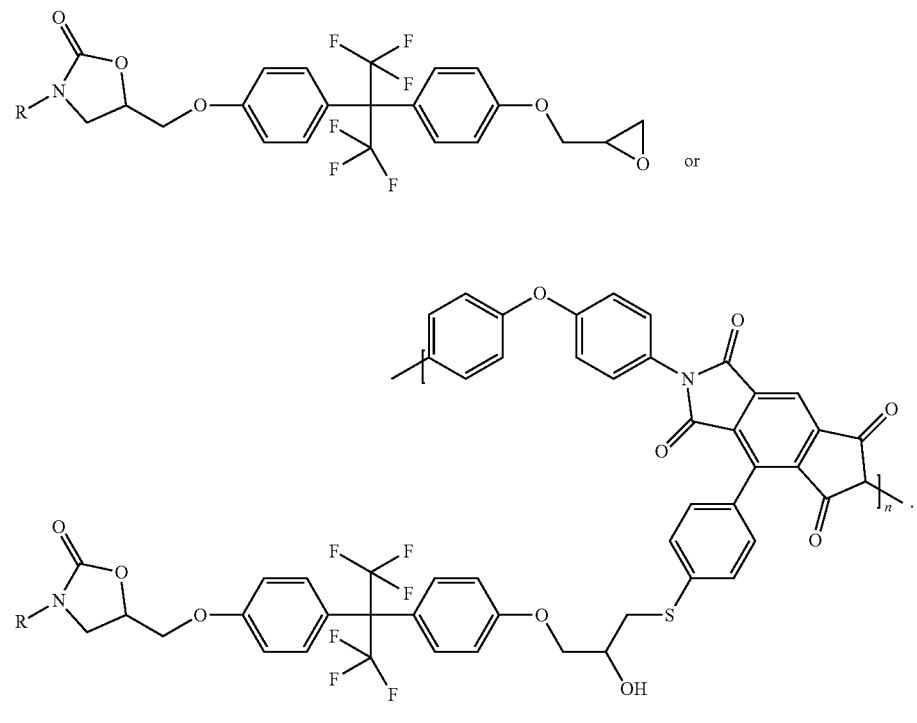

23. The system of claim 21 wherein the at least one conductive structure comprises at least one copper structure or at least one copper-containing alloy structure.

24. The system of claim 21 wherein the dielectric layer further comprises a filler material that includes one or more of the following: boron nitride (BN) and zirconium tungstate $(Zr(WO_4)_2)$.

25. A dielectric material having a dielectric constant (Dk) of less than or equal to 3 and a dissipation factor (Df) of less than or equal to 0.001 and comprising a compound that includes at least one of:

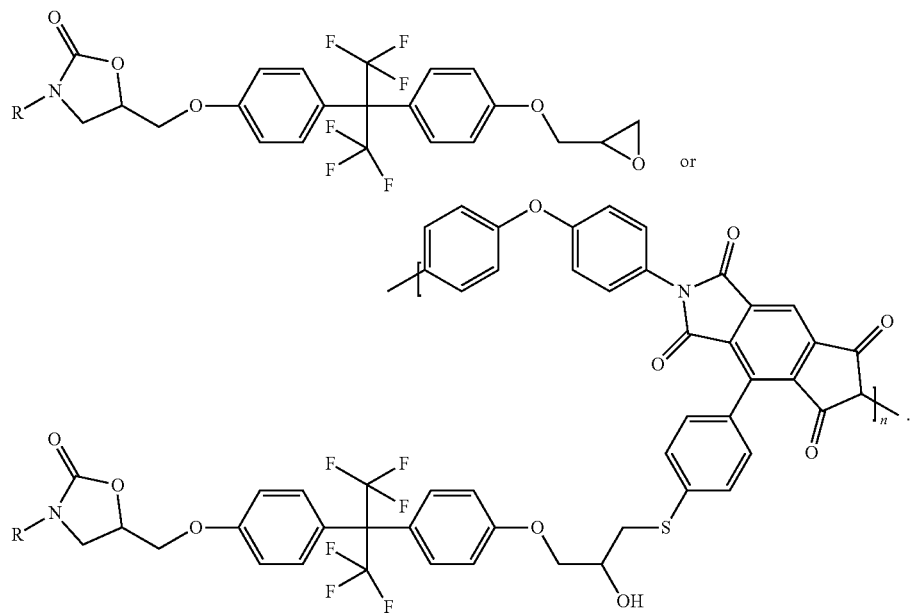
WHERE n > 3
* * * * *